United States Patent [19]

Harris et al.

[11] Patent Number: 5,693,511
[45] Date of Patent: Dec. 2, 1997

[54] IMMORTALIZED HUMAN FETAL OSTEOBLASTIC CELLS

[75] Inventors: Steven A. Harris; Thomas C. Spelsberg, both of Rochester, Minn.

[73] Assignee: Mayo Foundation for Medical Education and Research, Rochester, Minn.

[21] Appl. No.: 697,906

[22] Filed: Aug. 30, 1996

Related U.S. Application Data

[60] Division of Ser. No. 273,351, Jul. 11, 1994, which is a continuation-in-part of Ser. No. 89,848, Jul. 12, 1993.

[51] Int. Cl.$^6$ ............................................. C12N 15/90
[52] U.S. Cl. .................. 435/172.3; 435/366; 435/320.1
[58] Field of Search ......................... 435/6, 320.1, 240.2, 435/172.3, 366

[56] References Cited

FOREIGN PATENT DOCUMENTS

WO 89/09816  10/1989  WIPO.

OTHER PUBLICATIONS

Tora et al., *EMBO J.*, vol. 8, 1989, pp. 1981–1986.

*Current Protocols in Molecular Biology*, Eds., F. M. Ausubel et al., Eds, John Wiley & Sons: New York, NY 1989. This reference is cited at page 31, lines 26–28 of the present application. Enclosed is the Title page, Copyright page and Contents pages (pp. iii–x).

Y. Aoi, et al., "Newly Synthesized Glycoproteins in Plasma Membranes of Cells Transformed by SV40 and Its Gene A Function", *Tohoku J. Exp. Med.*, 131, 95–96, (1980).

M. A. Aronow, et al., "Factors That Promote Progressive Development of the Osteoblast Phenotype in Cultured Fetal Rat Calvaria Cells", *J. Cell. Physiol.*, 143, 213–221, (1990).

D. Barnes, et al., "Methods for Growth of Cultured Cells in Serum–Free Medium", *Anal. Biochem.*, 102, 255–270, (1980).

U.S. Barzel, "Estrogens in the Prevention and Treatment of Postmenopausal Osteoporosis: A Review", *Am. J. Med.*, 85, 847–850, (Dec. 1988).

M. Bodo, et al., "Effects of Steroids on Human Normal and otosclerotic Osteoblastic Cells: Influence on Thymidine and Leucine Uptake and Incorporation.", *Cellular and Molecular Biology 37*, 597–606, (1991).

M. M. Bradford, "A Rapid and Sensitive Method for the Quantitation of Microgram Quantities of Protein Utilizing the Principle of Protein–Dye Binding", *Anal Biochem.*, 72, 248–254, (1976).

J. S. Butel, et al., "Transformation of Primate and Rodent Cells by Temperature–sensitive Mutants of SV40", *Tumor Viruses*, 39, 25–36, (1975).

E. Canalis, et al., "Insulin–like growth factor I mediates selective anabolic effects of parathyroid hormone in bone cultures", *J. Clin. Invest.*, 83, 60–65, (Jan. 1989).

S. K. Chattopadhyay, et al., "Quantitative studies of integration of murine leukemia virus after exogenous infection", *Proc. Natl. Acad. Sci. USA*, 73, 4095–4099, (1976).

C. L. Chen, et al., "abstract of Characterization of endocrine cell lines immortalized by a temperature–sensitive mutant SV40", *Chinese J. Physiol.*, 34, 65–80, (1991).

H. Chiba, et al., "Establishment and Characterization of a Simian Virus 40–immortalized Osteoblastic Cell Line from Normal Human Bone", *Jpn. J. Cancer Res.*, 84, 290–297, (Mar. 1993).

P. Chomczynski, "A Reagent for the Single–Step Simultaneous Isolation of RNA, DNA and Proteins from Cell and Tissue Samples", *BioTechniques*, 15, 532–536, (1993).

J. Y. Chou, "Differentiated Mammalian Cell Lines Immortalized by Temperature–Sensitive Tumor Viruses", *Mol. Endocrinol.*, 3 1511–1514 (1989).

D. S. Colvard, et al., "Microassay for Nuclear Binding of Steroid Receptors with Use of Intact Cells from Small Samples of Arian and Human Tissue", *Clin. Chem.*, 34, 363–369, (1988).

J. A. DeCaprio, et al., "SV40 Large Tumor Antigen Forms a Specific Complex with the Product of the Retinoblastoma Susceptibility Gene", *Cell, 54*, 275–283, (Jul. 15, 1988).

E. F. Eriksen, et al., "Evidence of Estrogen Receptors in Normal Human Osteoblast–Like Cells", *Science, 241*, 84–86, (Jul. 1, 1988).

M. Ernst, et al., "Estradiol Effects on Proliferation, Messenger Ribonucleic Acid for Collagen and Insulin–like Growth Factor–I, and Parathyroid Hormone–Stimulated Adenylate Cyclase Activity in Osteoblastic Cells from Calvariae and Long Bones", *Endocrinology, 125,* 825–833, (1989).

M. C. Etienne, et al., "Steroid Receptors in Human Osteoblast–like Cells", *Eur. J. Cancer, 26,* 807–810, (1990).

C E Evans, et al., "Effects of two novel bisphosphonates on bond cells in vitro", *Bone and Mineral, 26,* 95–107, (1994).

W. Fiers, et al., "Complete nucleotide sequence of SV40 DNA", *Nature, 273,* 113–120, (May 11, 1978).

L. W. Fisher, et al., "Purification and Partial Characterization of Small Proteoglycans I and II, Bone Sialoproteins I and II, and Osteonectin from the Mineral Compartment of Developing Human Bone", *J. Biol. Chem., 262,* 9702–9708, (1987).

R. T. Franceschi, et al., "1α, 25–Dihydroxyvitamin D3 Specific Regulation of Growth, Morphology, and Fibronectin in a Human Osteosarcoma Cell Line", *J. Cell. Physiol., 123,* 401–409, (1985).

L. Fransen, et al., "Changes in Gene Expression and Protein Phosphorylation in Murine Cells, Transformed or Abortively Infected with Wild Type and Mutant Simian Virus 40", *J. Biol. Chem., 258,* 5276–5290, (1983).

T. K. Gray, et al., "17β–Estradiol acts directly on the clonal osteoblastic cell line UMR106", *Proc. Natl. Acad. Sci., 84,* 6267–6274, (1987).

T. K. Gray, et al., "Estradiol Stimulates in vitro the Secretion of Insulin–like Growth Factors by the Clonal Osteoblastic Cell Line UMR106", *Bioc. Biophys. Res. Comm., 158,* 407–412, (1989).

P. J. Greenaway, et al., "Human cytomegalovirus DNA: BamHI, EcoRI and PstI restriction endonuclease cleavage maps", *Gene, 28,* 355–360, (1982).

R. G. Ham, et al., "Media and Growth Requirements", *Methods Enzymol., 58,* 44–93, (1979).

S. A. Harris, et al., "Development and Characterization of a Conditionally–Transformed Human Fetal Osteoblastic Cell Line", *J. Bone Min. Res., 8,* Abstract No. 745, S303, (1993).

S. A. Harris, et al., "Development and Characterization of a Conditionally Immortilized Human Fetal Osteoblastic Cell Line", *J. Bone Min. Res.,* 1–14, (1993).

S. A. Harris, et al., "Development and Characterization of a Conditionally Immortalized Human Fetal Osteoblastic Cell Line", *J. Bone Miner. Res., 10,* 178–186, (1995).

S. A. Harris, et al., "Estrogen Induces C–FOS Promoter Activity in Normal Human Osteoblast–Like Cells", *J. Bone Min. Res., 7,* Abstract No. 7, (1992).

C. H. Heldin, et al., "A human osteosarcoma cell line secretes a growth factor structurally related to a homodimer of PDGF A–chains", *Nature, 319,* 511–514, (1986).

G. Helftenbein, et al., "Establishment of a temperature–dependent cell line from rat endometrium by retroviral infection", *Eur. J. Cell Biol., 56,* 49–57, (1991).

J. Imbert, et al., "Stabilization of the Large T Protein in Temperature–independent (Type A) FR 3T3 Rat Cells Transformed with the Simian Virus 40 tsA30 Mutant", *J. Virol., 47,* 442–451, (Sep. 1983).

H. C. Isom, et al., "Transformation of Isolated Rat Hepatocytes with Simian Virus 40", *J. Cell Biol, 85,* 651–659, (Jun. 1980).

R. L. Jilka, et al., "Increased Osteoclast Development After Estrogen Loss: Mediation by Interleukin–6", *Science, 257,* 88–91, (Jul. 3, 1992).

K. J. Kaneko, et al., "Activation of the Silent Progesterone Receptor Gene by Ectopic Expression of Estrogen Receptors in a Rat Fibroblast Cell Line", *Biochemistry, 32,* 8348–8359, (1993).

T. Katagiri, et al., "Bone morphogenetic protein–2 converts the differentiation pathway of C2C12 myoblasts into the osteoblast lineage.", *J. Cell Biol., 127,* 1755–1766, (Dec. 1994).

Katagiri, et al., "The non–osteogenic mouse pluripotent cell line, C3H10T1/2, is induced to differentiate into osteoblastic cells by recombinant human bone morphogenetic protein–2", *Biochem. Biophys. Res. Comm., 172,* 295–299, (Oct. 15, 1990).

P. E. Keeting, et al., "Development and Characterization of a Rapidly Proliferating, Well–Differentiated Cell Line Derived from Normal Adult Human Osteoblast–like Cells Transfected with SV40 Large T Antiget", *J. Bone Min. Res., 7,* 127–136, (Nov. 1992).

M. Kirstein, et al., "Tumor Necrosis Factor Stimulates Proliferation of Human Osteosarcoma Cells and Accumulation of c–myc Messenger RNA", *J. Cell. Physiol., 134,* 479–484, (1988).

B. S. Komm, "Estrogen Binding, Receptor mRNA, and Biologic Response in Osteoblast–Like Osteosarcoma Cells", *Science, 241,* 81–84, (Jul. 1, 1988).

J. Koniecki, et al., "Effect of the SV40 T Antigen on the Posttranscriptional Regulation of the Proliferating Cell Nuclear Antigen and DNA Polymerase–α Genes", *Cancer Research, 51,* 1465–1471, (Mar. 1, 1991).

C. Lafarge–Frayssinet, et al., "Expression of Gamma––Glutamyl Transpeptidase in Adult Rat Liver Cells After Transformation with SV40 Virus", *Cancer Letters, 22,* 31–39, (1984).

R. Langer. et al., "Tissue Engineering", *Science, 260,* 920–926, (May 14, 1993).

Y. Liel, et al., "Evidence That Estrogens Modulate Activity and Increase the Number of 1,25 Dihydroxyvitamin D Receptors in Osteoblast–Like Cells (ROS 17/2.8)", *Endocrinology, 130,* 2597–2601, (1992).

R. Lindsay, "The influence of cigarette smoking on bone mass and bone loss", *Osteoporosis: Recent Advances in Pathogenesis and Treatment;,* University Park Press: Baltimore, MD, 481, (1981).

C. Liu, et al., "Human parathyroid hormone–(1–34) prevents bone loss and augments bone formation in sexually mature overiectomized rats", *J. Bone Miner. Res., 5,* 973–982, (1990).

J. W. Ludlow, et al., "SV40 Large T Antigen Binds Preferentially to an Underphosphorylated Member of the Retinoblastoma Susceptibility Gene Product Family", *Cell, 56,* 57–65, (Jan. 13, 1989).

C. Marcelli, et al., "In vivo effects of human recombinant transforming growth factor β on bone turnover in normal mice", *J. Bone Miner. Res., 5,* 1087–1096, (1990).

T. J. Martin, et al , "Hormonal Influences on Bone Cells", *Methods Enzymol., 145,* 324–336, (1987).

A. Marusic, et al., "Production of Leukemia inhibitory factor mRNA and protein by malignant and immortalized bone cells", *Chem. Abs., 121,* Abstract No. 154804, (Sep. 24, 1994).

T Matsumura, et al "Studies of SV40–Infected Werner Syndrome Fibroblasts", *Adv. Exp. Med. Biol., 190,* 313–330, (1985).

A. M. Maxam, et al., "Sequencing End–Labeled DNA with Base–Specific Chemical Cleavages", *Methods Enzymol 65*, 499–560, (1980).

G. K. McMaster, et al., "Analysis of single– and double–stranded nucleic acids on polyacrylamide and agarose gels by using glyoxal and acridine orange", *Proc. Natl. Acad. Sci. USA, 74*, 4835–4838, (Nov. 1977).

J. Messing, et al., "A system for shotgun DNA sequencing", *Nucl. Acids Res., 9* 309–320, (1981).

S. Migliaccio, et al., "Estrogens Modulate the Responsiveness of Osteoblast–Like Cells (ROS 17/2.8) Stably Transfected with Estrogen Receptor", *Endocrinology, 130*, 2618–2624, (1992).

T. Mitsudomi, et al., "Abortive Transformation of Temperature–Sensitive Mutants of Rat 3Y1 Cells by Simian Virus 40: Effect of Cellular Arrest States on Entry Into S Phase and Cellular Proliferation", *J. Cell. Physiol., 123*, 353–360, (1985).

R. C. Mulligan, et al., "Expression of a Bacterial Gene in Mammalian Cells", *Science, 209*, 1422–1427, (1980).

T. M. Murray, et al., "Human parathyroid hormone carboxy–terminal peptide (53–84) stimulates alkaline phosphatase activity in dexamethasone–treated rat osteosarcoma cells in vitro", *Endocrinology, 124*, 1097–1099, (Feb. 1989).

D. S. Neufeld, et al., "Immortalization of Human Fibroblasts Transformed by Origin–Defective Simian Virus 40", *Mol. Cell. Biol., 7*, 2794–2802, (Aug. 1987).

M. Noda, et al., "In vivo stimulation of bone formation by transforming growth factor–$\beta$.", *Endocrinology, 124*, 2991–2994, (May 1989).

C. A. Noonan, et al., "Characterization of Simian Cells Transformed by Temperature–Sensitive Mutants of Simian Virus 40", *J. Virol., 18*, 1106–1119, (Jun. 1976).

K. Onodera, et al., "Alterations in surface glycoproteins and level of sialyltransferase of cells transformed by a temperature–sensitive mutant of simian virus 40", *Proc. Natl. Acad. Sci. USA, 73*, 4090–4094, (Nov. 1976).

M. J. Oursler, et al., "Modulation of Transforming Growth Factor–$\beta$ Production in Normal Human Osteoblast–Like Cells by 17$\beta$–Estradiol and Parathyroid Hormone", *Endocrinology, 129*, 3313–3320 (1991).

T. A. Owen, et al., "Coordinate occupancy of AP–1 sites in the vitamin D–responsive and CCAAT box elements by Fos–Jun in the osteocalcin gene: Model for phenotype suppression of transcription", *Proc. Natl. Acad. Sci. USA, 87*, 9990–9995, (Dec. 1990).

R. Pacifici, et al., "Ovarian steroid treatment blocks a postmenopausal increase in blood monocyte interleukin 1 release", *Proc. Natl. Acad. Sci. USA, 86*, 2398–2402, (Apr. 1989).

G. Passeri, et al., "Increased Interleukin–6 Production by Murine Bone Marrow and Bone Cells after Estrogen Withdrawal", *Endrocrinology, 133*, 822–828, (1993).

G. N. Pavlakis, et al., "Expression of two human growth hormone genes in monkey cells infected by simian virus 40 recombinants", *Proc. Natl. Acad. Sci. USA, 78*, 7398–7402, (Dec. 1981).

W. A. Peck, et al., "Evidence for Preferential Effects of Parathyroid Hormone, Calcitonin and Adenosine on Bone and Periosteum", *Endocrinology, 100*, 1357–1364, (1977).

J. Pfeilschifter, et al., "Stimulation of Bone Matrix Apposition in Vitro by Local Growth Factors: A Comparison between insulin–like Growth Factor I, Platelet–Derived Growth Factor, and Tranforming Growth Factor $\beta$", *Endocrinology 127*, 69–75, (1990).

L A Pivirotto, et al., "Sex hormones mediate interleukin–1$\beta$ production by human osteoblastic HOBIT cells", *Mol. Cell. Endocrinol., 111*, 67–74, (1995).

J. S. Price, et al., "The Cell Biology of Bone Growth", *Eur. J. Clin. Nutr., 48 Suppl. 1*, ABSTRACT Only, S131–S149, (Feb. 1994).

L. D. Quarles, "Paradoxical Toxic and Trophic Osseous Actions of Aluminum: Potential Explanations", *Miner. Electroylte Metab., 17*, 233–239, (1991).

V. B. Reddy, et al., "The Genome of Simian Virus 40", *Science, 200*, 494–502, (May 5, 1978).

J. Reeve, et al., "Anabolic effect of human parathyroid hormone fragment on trabecular bone in involutional osteoporosis: a multicentre trial", *Brit. Med. J., 280*, 1340–1344, (Jun. 7, 1980).

A. J. Ridley, et al., "ras–Mediated cell cycle arrest is altered by nuclear oncogenes to induce Schwann cell transformation", *EMBO J., 7*, 1635–1645, (1988).

B. L. Riggs, et al., "Short– and Long–Term Effects of Estrogen and Synthetic Anabolic Hormone in Postmenopausal Osteoporosis", *J. Clin. Investigation, 51*, (Jul. 1972).

C. A. Rinehart, et al., "Alterations of DNA content in human endometrial stromal cells transfected with a temperature––sensitive SV40: tetraploidization and physiological consequences", *Carcinogenesis, 13*, 63–68, (1992).

P. G. Robey, et al., "Human Bone Cells In Vitro", *Calcif. Tissue Int., 37*, 453–460, (1985).

P. G. Robey, et al., "Osteoblasts synthesize and respond to transforming growth factor–type $\beta$ (TGF–$\beta$) in vitro", *J. Cell Biol. 105*, 457–463, (Jul. 1987).

S. B. Rodan, et al., "Characterization of a Human Osteosarcoma Cell Line (Saos–2) with Osteoblastic Properties", *Cancer Res., 47*, 4961–4966, (Sep. 15, 1987).

G. A. Rodan, et al., "Expression of the Osteoblastic Phenotype", *Bone and Mineral Research*, W. A. Peck, Ed.; Elsevier, Amsterdam, 244–285, (1983).

G. A. Rodan, et al., "Gene Expression in Osteoblastic Cells", *Crit. Rev. Eukaryot. Gene Expr., 1*, 85–98, (1991).

H. Rothschild, et al., "Isolation and Characterization of a Heat–Inducible Simian Virus 40 Mutant", *J. Virol., 19*, 374–381, (Aug. 1976).

P. Sassone–Corsi, et al., "Transcriptional autoregulation of the proto–oncogene fos", *Nature, 334*, 314–319, (Jul. 1988).

R. K. Schenk, et al., "Preparation of calcified tissues for light microscopy", *Methods of Calcified Tissue Preparation*, G. R. Dickson, Ed.; Elsevier, Amsterdam, 1–56, (1984).

D. M. Slovik, et al., "Short–term effects of synthetic human parathyroid hormone–(1–34) administration on bone mineral metabolism in osteoporotic patients.", *J. Clin. Invest., 68*, 1261–1271, (Nov. 1981).

P. J. Southern, et al., "Transformation of Mammalian Cells to Antibiotic Resistance with a Bacterial Gene Under Control of the SV40 Early Region Promoter", *J. Mol. Appl. Gen., 1*, 327–341, (1982).

T. C. Spelsberg, "Bone Cell Proto–Oncogene Promoters", Abstract, National Institutes of Health Grant No. AR41652.

T. C. Spelsberg; "Sex Steroids, Growth Factors and Bone Cell Function", Abstract, National Institutes of Health Grant No. AG04875.

J. L. Spurbeck, et al., "Culturing and Robotic Harvesting of Bone Marrow, Lymph Nodes, Peripheral Blood, Fibroblasts, and Solid Tumors with in situ Techniques", *Cancer Genet. Cytogenet., 32*, 59–66, (1988).

G. S. Stein, et al., "Relationship of cell growth to the regulation of tissue-specific gene expression during osteoblast differentiation", *FASEB J., 4,* 3111–3123, (Oct. 1990).

B. Sugden, et al., "A Vector That Replicates as a Plasmid and Can be Efficiently Selected in B–Lymphoblasts Transformed by Epstein–Barr Virus", *Mol. Cell. Biol., 5,* 410–413, (Feb. 1985).

P. Tegtmeyer, et al., "Function of Simian Virus 40 Gene A in Transforming infection", *J. Virol., 15,* 613–618, (Mar. 1975).

S. N. Thibodeau, et al., "Simultaneous Measurement of Estrogen and progesterone Receptors in Tumor Cytosols with Use of 125I–Labeled Estradiol and of 3H–R5020", *Clin. Chem., 27,* 687–691, (1981).

R. S. Thies, et al., "Recombinant human bone morphogenetic protein–2 induces osteoblastic differentiation in W–20–17 stromal cells", *Endocrinology, 130,* 1318–1324, (Mar. 1992).

D. R. Thomsen, "Promoter–regulatory region of the major immediate early gene of human cytomegalovirus", *Proc. Natl. Acad. Sci. USA, 81,* 659–663, (Feb. 1984).

L. Tora, et al., "The cloned human oestrogen receptor contains a mutation which alters its hormone binding properties", *EMBO J., 8,* 1981–1986, (1989).

H. Tsuchiya, et al., "Differentiating and Antitumor Activities of 1α, 25–Dihydroxyvitamin D3 In Vitro and 1α–Hydroxyvitamin D3 In Vitro on Human Osteosarcoma.", *J. Orthopaedic Res. 11,* 122–130, (1993).

G. Van der Pluijm, et al., "Disodium 1–Hydroxy–3–(1–Pyrrolidinyl)–Propylidene–1, 1–Bisphosphonate (EB–1053) Is a Potent Inhibitor of Bone Resorption In Vitro", *J. Bone Min. Res., 7,* 981–986, (1992).

E. A. Wang, et al., "Recombinant human bone morphogenetic protein induces bone formation", *Proc. Natl. Acad. Sci. USA, 87,* 2220–2224, (Mar. 1990).

C. K. W. Watts, et al., "Stable Transfection of the Oestrogen Receptor Gene into a Human Osteosarcoma Cell Line", *J. Steroid Biochem., 34,* 483–490, (1989).

A. Weisz, et al., "Estrogen Induces Expression of c–fos and c–myc Protooncogenes in Rat Uterus", *Mol. Endocrinol., 2,* 816–824, (Sep. 1988).

A. Weisz, et al., "Identification of an estrogen response element upstream of the human c–fos gene that binds the estrogen receptor and the AP–1 transcription factor", *Nucl. Acids Res., 18,* 5097–5106, (1990).

G. Wilding, et al., "Effects of Steroid Hormones and Peptides Growth Factors on Protooncogene c–fos Expression in Human Breast Cancer Cells", *Cancer Res., 48,* 802–805, (Feb. 15, 1988).

J. M. Wozney, et al., "Novel regulators of bone formation: Molecular clones and activities", *Science, 242,* 1528–1534, (1988).

D. Wynford–Thomas, et al., "Conditional Immortalization of Human Thyroid Epithelial Cells: A tool for Analysis of Oncogene Action", *Mol. Cell Biol., 10,* 5365–5377, (Oct. 1990).

A. Yamaguchi, et al., "Recombinant human bone morphogenetic protein–2 stimulates osteoblastic maturation and inhibits myogenic differentiation in vitro", *J. Cell Biol, 113,* 681–687 (May 1991).

S. H. Zuckerman, et al., "Transformation–Associated Changes in Nuclear–Coded Mitochondrial Proteins in 3T3 Cells and SV40–Transformed 3T3 Cells", *Bioc. Biophys. Acta, 804,* 285–290, (1984).

*Primary Examiner*—James Ketter
*Attorney, Agent, or Firm*—Schwegman, Lundberg, Woessner & Kluth, P.A.

[57] ABSTRACT

Immortalized normal human fetal osteoblastic cells that express a temperature sensitive mutant of simian virus 40 large T antigen are provided.

25 Claims, 25 Drawing Sheets

IMMORTALIZED HUMAN FETAL OSTEOBLASTIC CELLS

CROSS-REFERENCE TO RELATED APPLICATION

This application is a division of U.S. patent application Ser. No. 08/273,351, filed Jul. 11, 1994, which in turn is a continuation-in-part of U.S. Ser. No. 08/089,848, filed Jul. 12, 1993, which is incorporated herein by reference.

STATEMENT OF GOVERNMENT RIGHTS

This invention was made with the support of the U.S. Government under National Institutes of Health Grant Nos. AR41652 and AG04875. The Government has certain rights in the invention.

BACKGROUND OF THE INVENTION

Postmenopausal osteoporosis is a condition that affects millions of women and results in debilitating bone and spinal injuries. This condition is characterized by dramatic bone deterioration due to an imbalance between bone formation (by osteoblasts) and bone resorption (by osteoclasts). Osteoblasts are cells that arise from connective tissue precursor cells in bone marrow, and are associated with bone growth as they mature. Osteoclasts are cells associated with the absorption and removal of bone. In normal bone, the balance between osteoblast-mediated bone formation and osteoclast-mediated bone resorption is maintained through complex cell to cell interactions. To determine the causes for bone deterioration associated with osteoporosis, and to devise effective treatments for this condition, the processes of osteoblast differentiation, osteoblast physiology, osteoblast-osteoclast communication, and osteoclast function must be studied further.

A number of model systems utilizing osteoblastic cells in culture have been developed to gain further insight into the process of bone formation. The most widely used cultured osteoblastic cells include primary cultures, i.e., cell cultures made by direct transfer from a natural source to an artificial medium. These cell cultures can be derived from normal human and rodent bone tissue, as well as from osteosarcoma cells obtained from adult human and rodent tumors. See, for example, P. G. Robey et al., *Calcif. Tissue Int.*, 37, 453 (1985); W. A. Peck et al., *Endocrinology*, 100, 1357 (1977); R. T. Franceschi et al., *J. Cell Physiol.*, 123, 401 (1985); C. H. Heldin et al., *Nature*, 319, 511 (1986); S. B. Rodan et al., *Cancer Res.*, 47, 4961 (1987); M. Kirstein et al., *J. Cell Physiol.*, 134, 479 (1988); G. A. Rodan et al., in *Bone and Mineral Research*; W. A. Peck, Eds.; Elsevier: 244 (1984); and T. J. Martin et al., *Methods Enzymol.*, 145, 324 (1987). These model systems, as well as other osteoblastic cell systems, have contributed greatly to the understanding of osteoblast biology. However, each of these model systems has limitations with regard to its application to the study of human osteoblast biology and hormones, such as estrogen, or growth factors. Furthermore, these model systems cannot be used in methods of treating a human for bone loss.

Osteoblastic cultures derived from rodent species are problematic because they may exhibit species-specific phenotypic characteristics which differ from those of human osteoblastic cultures. Osteosarcoma cells proliferate rapidly in culture but are inadequate because they have a different phenotype than untransformed cells, and an unknown genetic transforming event (G. A. Rodan et al., *Crit. Rev. Eukaryot. Gene Expr.*, 1, 85 (1991)). Thus, these cells may respond abnormally to hormone or growth factor treatment. Primary cultures derived from normal adult human bone have a normal osteoblastic phenotype but proliferate at a very slow rate and become senescent after a relatively short time in culture. Thus, as a result of the slow growth and limited life span in culture, these cells too are of limited utility.

To avert the limitations of these cell systems, HOBIT (human osteoblast-like initial transfectant) cells were developed. These cells were derived from primary cultures of adult human bone cells transfected with a gene expressing the viral protein, SV40 large T antigen (P. E. Keeting et al., *J. Bone Min. Res.*, 7, 127 (1992)). Other laboratories have reported the establishment of human bone cell primary cultures infected with SV40 virus itself (H. Chiba et al., *Jpn. J. Cancer Res.*, 84, 290 (1993)). Although these latter cells were developed from normal fetal bone cells, they are not homogeneous populations. Furthermore, while these adult and fetal SV40-transformed cells express many osteoblast phenotypic markers, the expression of the SV40 large T antigen (T Ag) is constitutive, and thus cannot be manipulated. The utility of osteoblastic cells infected with wild type SV40 virus is further limited by other considerations, such as nonclonal derivation and the expression of other vital proteins. As a result, variations in phenotype within cell subpopulations may exist, or phenotypic changes induced by viral infection may occur.

The beneficial effects of estrogen in the treatment of bone loss in postmenopausal osteoporosis are well established. R. Lindsay, *Osteoporosis: Recent Advances in Pathogenesis and Treatment*; University Park Press: Baltimore, Md.; 481 (1981); B. L. Riggs et al., *J. Clin. Invest.*, 51, 1659–1663 (1972); and U. S. Barzel, *Am. J. Med.*, 85, 847–850 (1988). However, the mechanisms involved in the direct action of estrogen on human bone cells remain unclear. Low levels of estrogen receptor expression have been detected in cultured normal human osteoblastic cells as well as certain human and rat osteosarcoma cell lines. However, because bone remodeling does not occur in rodents, it is unclear whether estrogen effects on gene expression observed in rodent model systems can be extrapolated to humans. In addition, other species-specific differences may exist with regard to the cellular responses to estrogen treatment. Human osteosarcoma cells proliferate rapidly in culture, but do not display contact inhibition, nor do they exhibit the full range phenotypic characteristics associated with normal osteoblastic cells. Human osteoblastic cells are phenotypically normal and display contact inhibition, yet proliferate very slowly and can only be maintained in culture for a short time. The ability to study the effects of estrogen treatment directly on human osteoblastic cells is therefore also limited by the lack of a rapidly proliferating, yet phenotypically normal osteoblastic cell model.

Thus, what is needed are osteoblastic cells derived from normal human cells that overcome these disadvantages. Specifically, what is needed are phenotypically normal osteoblastic cells that could be cultured indefinitely, proliferate rapidly, and be propagated continually using routine cell culture techniques.

SUMMARY OF THE INVENTION

The present invention provides immortalized normal human fetal osteoblastic (hFOB) cells. As used herein, "immortal" or "immortalized" cells refer to a substantially continuous and permanently established cell culture with substantially unlimited cell division potential. That is, the cells can be cultured substantially indefinitely, i.e., for at least about 6 months under rapid conditions of growth, preferably much longer under slower growth conditions, and can be propagated rapidly and continually using routine cell culture techniques. Alternatively stated, the cells of the present invention can be cultured for at least about 100 population doublings. These cells produce a complement of proteins characteristic of normal human osteoblastic cells and are capable of osteoblastic differentiation. They can be used in cell culture studies of osteoblastic cell sensitivity to various agents, such as hormones, cytokines, and growth factors, or in tissue therapy.

Specifically, the present invention provides immortalized human fetal osteoblastic cells which express a temperature sensitive (ts) mutant of simian virus 40 (SV40) large T antigen (T Ag). These cells are part of an established "cell line;" however, they are generally nontumorogenic, i.e., they do not form tumors in mammals. They are preferably part of a homogeneous population. More preferably, the homogeneous population is a clonal population. As used herein, "clonal" cells refer to a homogeneous population of cells derived from a single progenitor cell.

In one embodiment of the invention, human fetal bone cells, isolated from human fetal tissue, are transfected with a gene coding for a temperature-sensitive mutant of SV40 large T antigen to yield immortalized human fetal osteoblastic cells, designated herein as hFOB 1.19. As used herein, "transfection" refers to a process by which foreign DNA is introduced into eucaryotic cells and expressed. The foreign DNA is typically included in an expression vector, such as a circular or linearized plasmid vector. In the preparation of a preferred embodiment of the present invention, human fetal bone cells are transfected by electroporation with the expression vector pUCSVtsA58. Additionally, the human fetal tissue cells can be transfected with a selectable marker gene, such as a gene coding for resistance to an agent normally toxic to the untransformed cells, such as an antibiotic, an antineoplastic agent, or an herbicide. In the preparation of another preferred embodiment of the present invention, human fetal bone cells transfected with a gene for ts mutant of SV40 T Ag are also transfected with the expression vector pSV2neo.

Although the cells of the present invention are prepared by transfecting with the gene coding for a temperature-sensitive mutant of the SV40 large T antigen that is incorporated into the expression vector pUCSVtsA58, gene fragments or mutations of this gene can be used as long as they impart temperature regulation to the resultant immortalized cells as defined herein. In addition, other genes that impart temperature regulation to the resultant cells can be used.

Although the cells of the present invention are referred to as immortalized, they could alternatively be referred to as transfected or transformed. Advantageously, they are normal cells that are conditionally immortalized. By this it is meant that the large T antigen is capable of being inactivated. Although the cells are still viable and express proteins, they can be put into a state of low proliferation. That is, preferred immortalized human fetal osteoblastic cells of the present invention can undergo rapid cell division, or little or no cell division as a result of inactivating the large T antigen. This inactivation can occur by increasing the temperature of incubation of the cell cultures. For example, at a temperature at or less than about 37° C., preferably about 33°–36° C., rapid cell division occurs, whereas at a temperature above about 37° C. little or no cell division occurs. Rather, differentiation occurs at elevated temperatures. Preferably and advantageously, the cells of the present invention can be cycled between an active and an inactive state, i.e., the large T antigen can be cyclicly activated and inactivated. In this way, cells of different phenotypes can be propagated from the immortalized normal human fetal cells of the present invention.

The preferred cells of the present invention have the identifying characteristics of ATCC CRL 11372. That is, they are clonal, conditionally immortalized normal human fetal cells capable of osteoblastic differentiation. They differ from transformed osteosarcoma cells in that they have the ability to differentiate into mature osteoblasts expressing the normal osteoblast phenotype. Thus, the cells of the present invention provide a homogenous, rapidly proliferating model system for studying normal human osteoblast differentiation, osteoblast physiology, and hormonal, growth factor, and other cytokine effects on osteoblast function and osteoblast differentiation.

The immortalized cells of the present invention express very low levels of the estrogen receptor, i.e., less than about 200 activated receptors per nucleus. "Activated receptors per nucleus" is a measure of the number of estrogen receptors that are capable of binding 17β-estradiol and translocating to the cell nucleus. The number of activated receptors per nucleus is determined by the micro nuclear binding assay. D. S. Colvard et al., *Clin. Chem.*, 34, 363–369 (1988). It is assumed that the mount of bound 17β-estradiol detected in this assay is equivalent to the number of functional estrogen receptors, i.e., the ligand/receptor stoichiometry is 1:1. The cells of the present invention can be transfected with a gene coding for human wild-type estrogen receptor. Transfected cells express human estrogen receptor at a level of at least about 400, preferably at least about 800, activated receptors per nucleus. Significantly, these cells are responsive to estrogen treatment. The establishment of these estrogen responsive human fetal osteoblastic cells provides a model system for the study of estrogen action on osteoblast physiology, differentiation, and function, e.g., cytokine and growth factor production.

The estrogen responsive human fetal osteoblastic cells of the present invention can be prepared from the immortalized normal human fetal cells of the present invention and any replicable expression vector containing a gene coding for human estrogen receptor. In a preferred embodiment of this invention, this expression vector is a plasmid, preferably a plasmid having the identifying characteristics of plasmid pHEGO-HYG, which is described in further detail in the examples.

Accordingly, another aspect of the present invention provides a method of testing a drug, i.e., a biological or chemical agent, for effects on osteoblastic cell physiology. This method involves exposing a culture of immortalized normal human fetal osteoblastic cells which express a temperature sensitive mutant of simian virus 40 large T antigen to the drug and monitoring at least one of the resultant changes in the physiology of the cultured cells. These cellular changes can be any of a variety of changes of interest. This includes, for example, monitoring secretion of growth factors and other cytokines, growth of osteoblastic cells, expression of osteoblast associated genes, formation of mineralized nodules, mineralization of an extracellular matrix, or formation of bone. If the drug under investigation is added to a culture of cells of the present invention at various incubation temperatures, its effect on different osteoblastic phenotypes can be investigated. For example, if the cells are incubated at a restrictive temperature, i.e., greater than about 37° C., preferably greater than about 38° C., and more preferably greater than about 39° C., cell division is slowed, differentiation increases, and a more mature osteoblast phenotype is produced. Thus, preferred embodiments of the present invention include adding a drug for evaluation to a culture of immortalized human fetal undifferentiated osteoblastic cells wherein the cells are cultured at a temperature no greater than about 37° C. Alternatively, a drug can be added to a culture of cells wherein the cells are cultured at a temperature greater than about 37° C. for evaluation of the drugs effect on a different phenotype, e.g., more mature phenotype, of the cells.

Furthermore, the present invention is directed to a method of treating bone loss in a mammal, e.g., a human. This method involves placing immortalized human fetal osteoblastic cells which express a temperature sensitive mutant of simian virus 40 large T antigen into or onto a deteriorated bone at the point of deterioration. As used herein, "deteriorated bone" refers to one that has deteriorated as a result of osteoporosis, bone fracture, bone break, or bone loss around a surgical implant. The cells are placed into the bone at the point of deterioration, fracture, or break in an amount effective to cause or induce new bone formation/replacement.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 1:
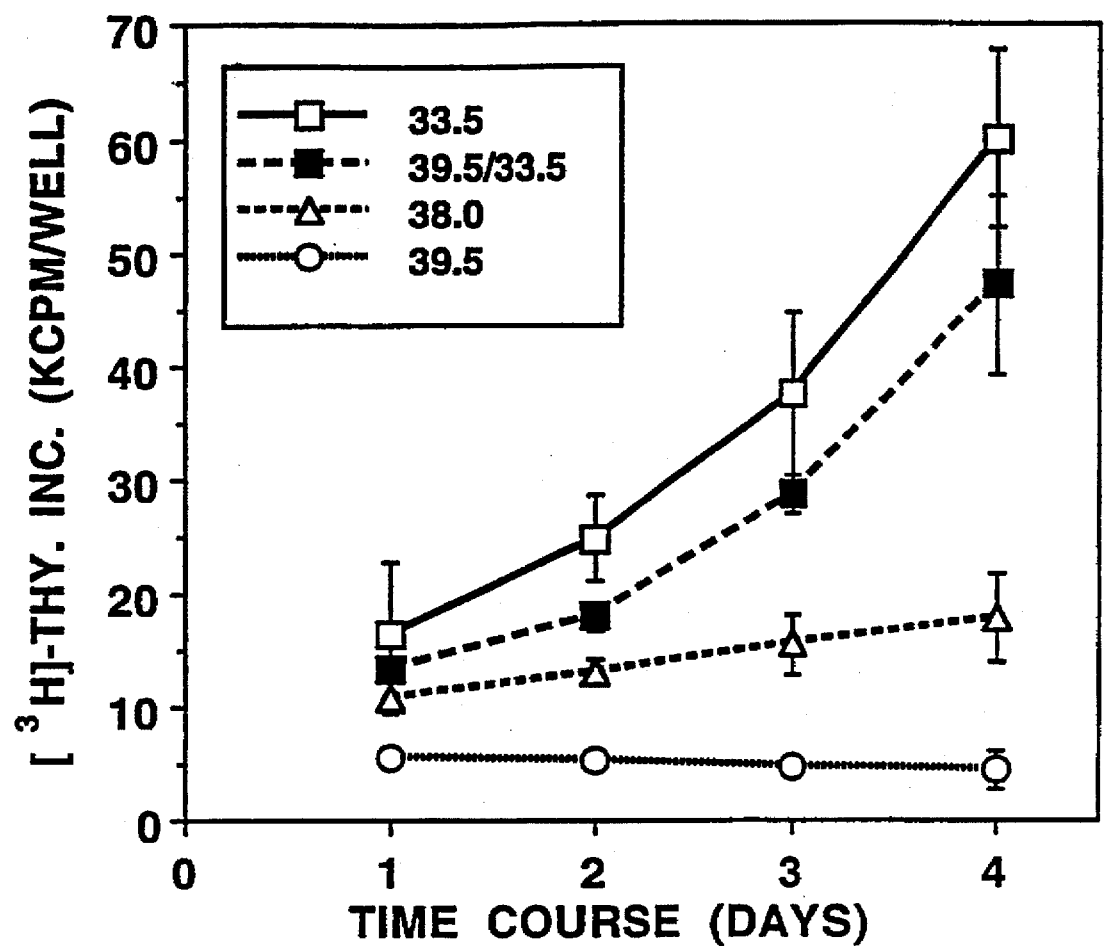
FIG. 1. Thymidine incorporation of hFOB 1.19 cells cultured at various temperatures. Subconfluent hFOB cultures were cultured at the indicated temperatures for 24 hours, then pulsed with $^3$H-labeled thymidine for 24 hours for each day of the time course, except that the designation 39.5/33.5 indicates that the cells were cultured at 39.5° C. for 24 hours, then returned to 33.5° C. for the remainder of the time course. Thymidine incorporation was measured after each pulse labelling. Error bars=1 standard deviation, n=4.
Figure 2A:
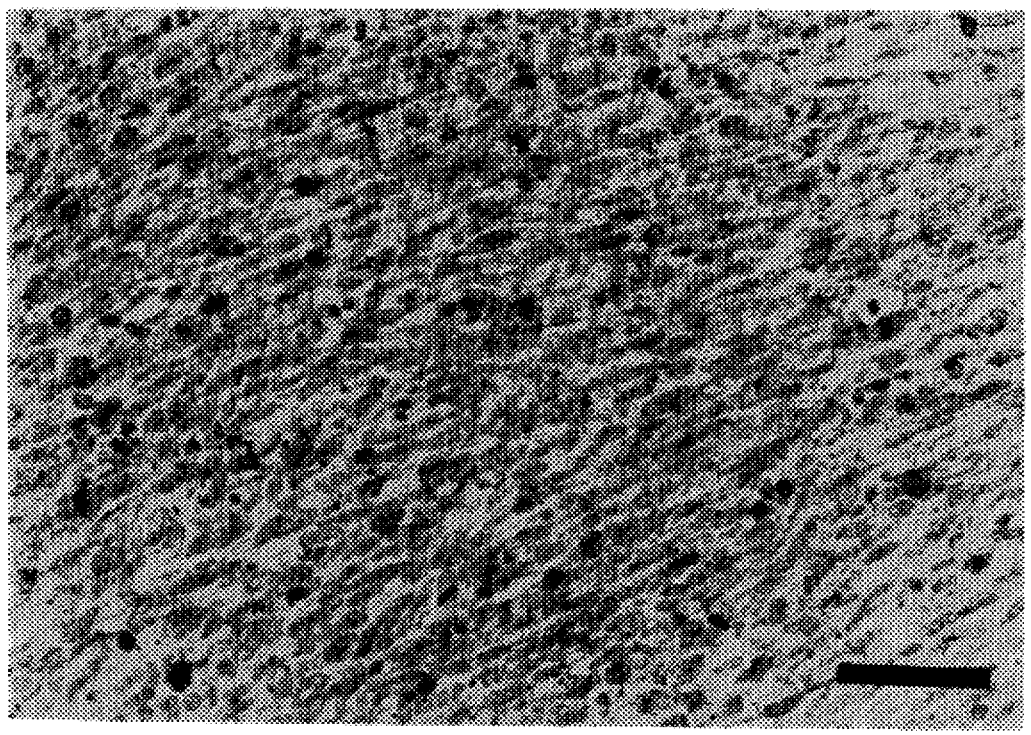
FIGS 2A–2H. Immunostaining of postconfluent hFOB 1.19 cells for osteoblast phenotypic markers. Postconfluent (day 8 after confluence) hFOB 1.19 cells cultured at 33.5° C. were stained by an immunoperoxidase method using primary antibodies (Ab) specific to: (A) osteopontin (OP); (B) osteonectin (ON); (C) osteocalcin (OC); (D) bone sialoprotein (BSP); (E) type I collagen; (F) no primary Ab; (G) SV40 T Ag; and (H) no primary Ab for T Ag. Dark (i.e., red) staining indicates areas where each protein (bound by Ab) is localized (100× magnification).
Figure 2B:
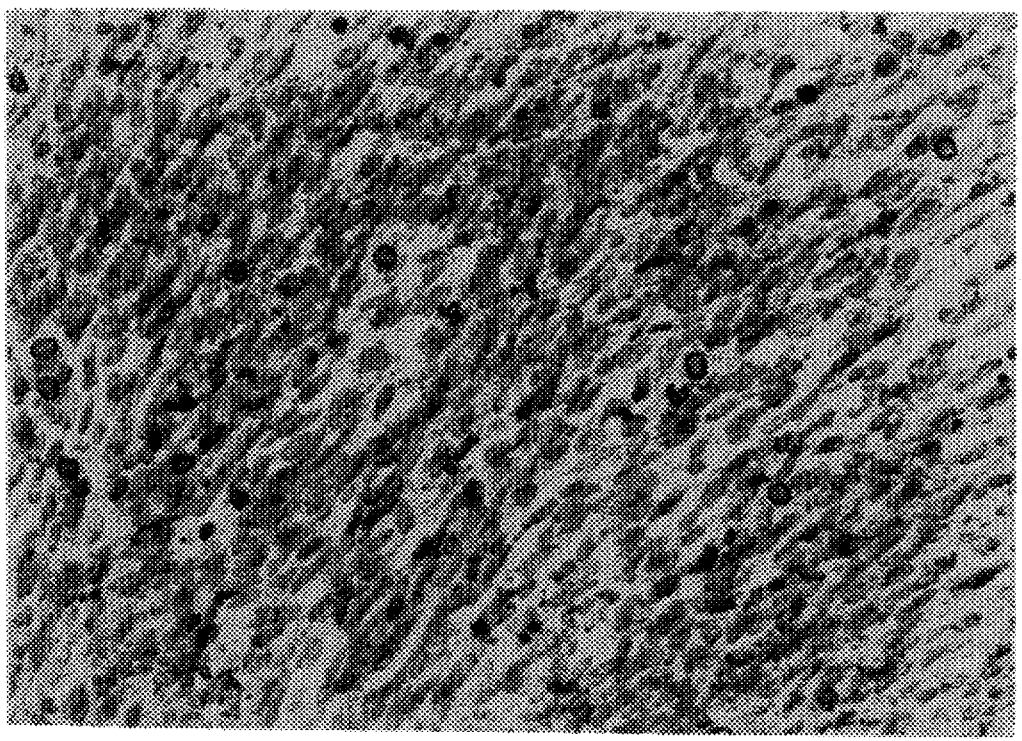
Figure 2C:
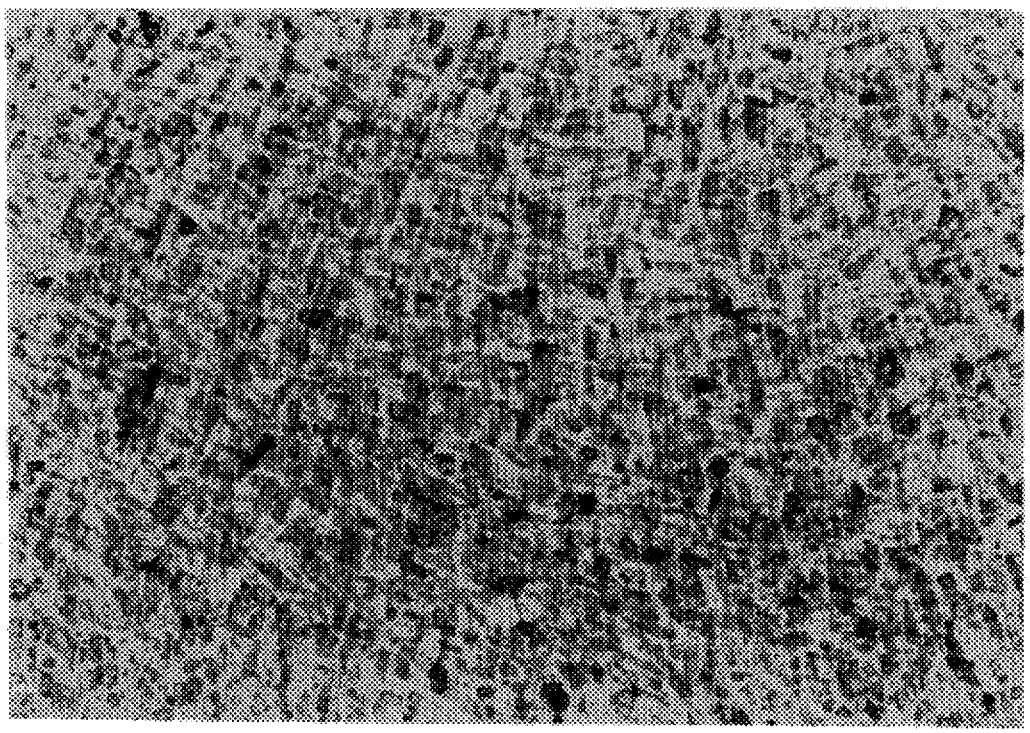
Figure 2D:
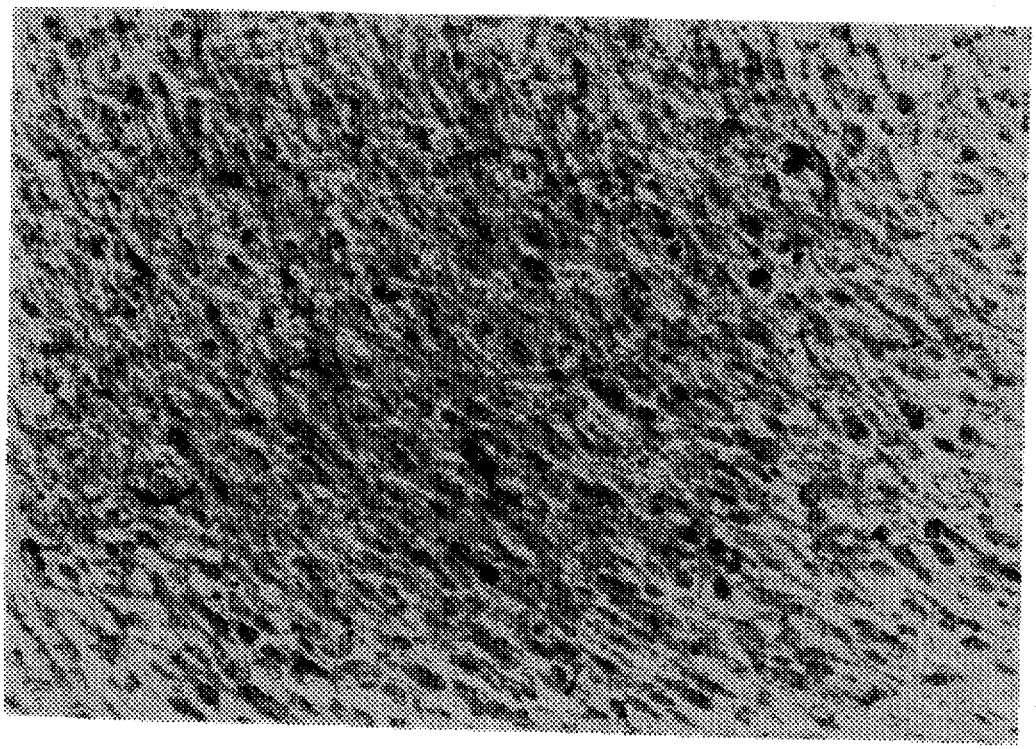
Figure 2E:
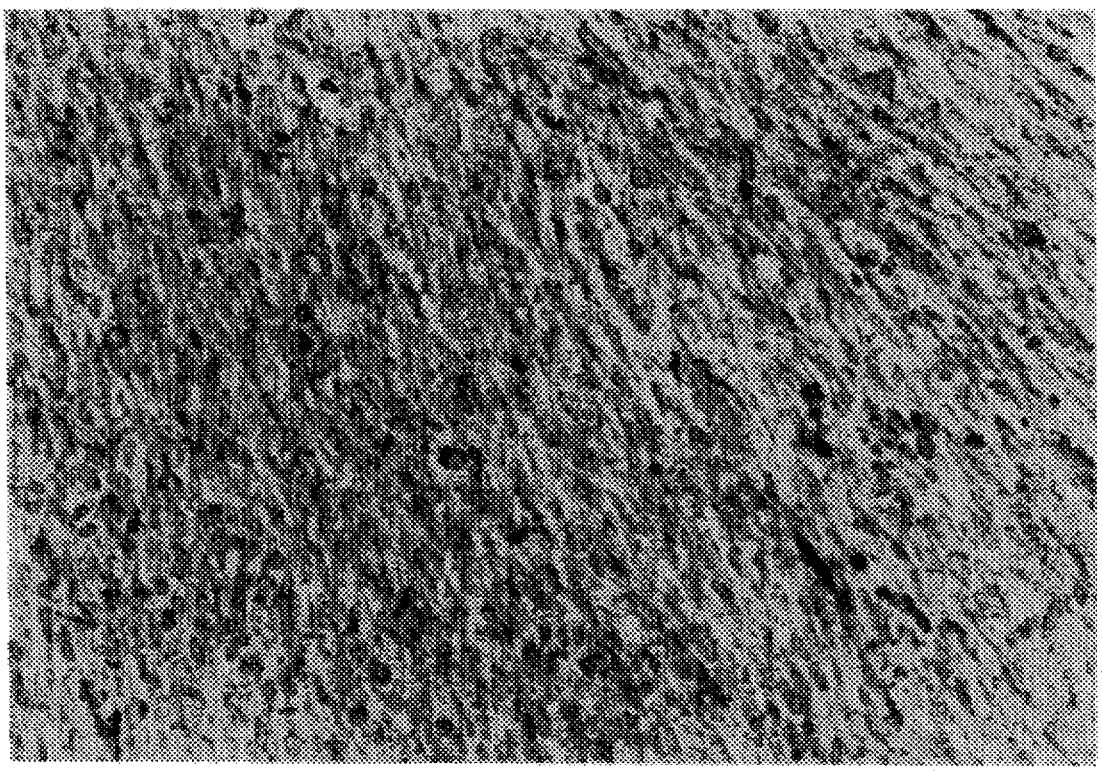
Figure 2F:
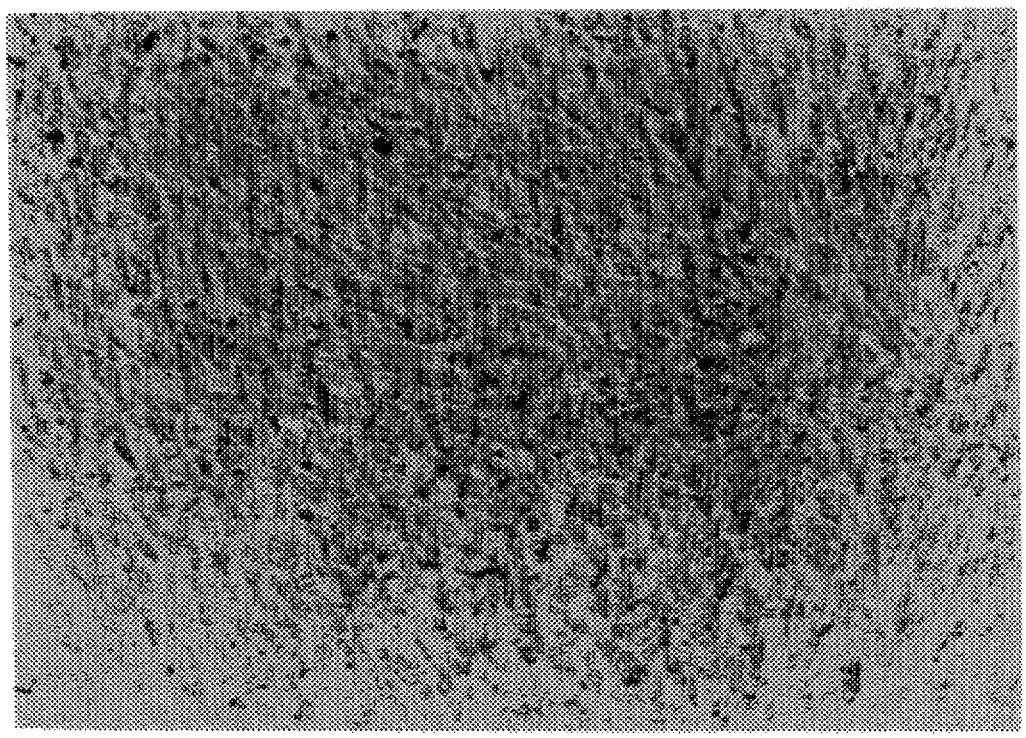
Figure 2G:
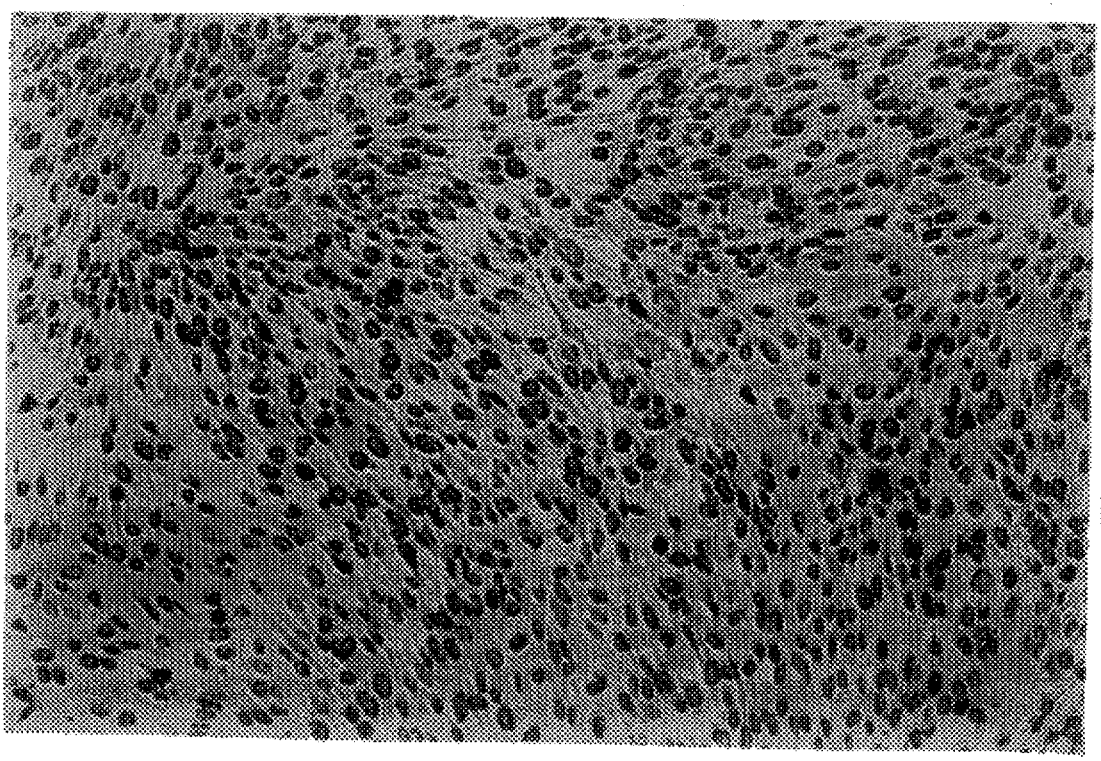
Figure 2H:
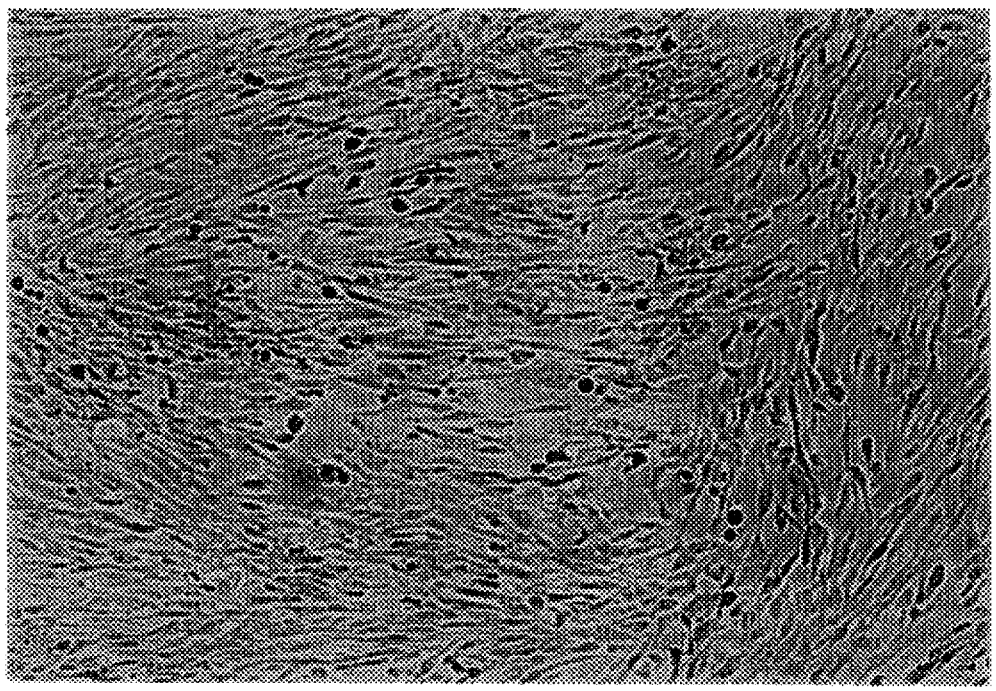

The present invention is directed to human normal fetal osteoblastic cells that are conditionally immortalized with a gene coding for a temperature-sensitive (ts) mutant (tsA58) of SV40 large T antigen (T Ag). This gene product, termed early gene or large T antigen, is responsible for immortalizing cells; however, the mechanism by which this occurs is unknown. The expression vector alone has no effect. Expression of T Ag in human cells results in an increased and prolonged rate of proliferation, which is believed to result from interaction of T Ag with the retinoblastoma gene product, Rb. Under conditional immortalization, however, the mutant T Ag is only active (i.e., the cells are immortalized) at a temperature referred to herein as "permissive" temperature. Thus, the return to an inactive (nonimmortalized) state can be manipulated by changing the incubation of the cells to a restrictive (nonpermissive) temperature. This type of conditional immortalization has been used successfully in other cell types. See, for example, J. Y. Chou, *Mol. Endocrinol.*, 3, 1511 (1989).

Thymidine incorporation experiments indicate that expression of this gene at the permissive temperature, which is at or less than about 37° C., preferably about 33°–36° C., and more preferably at a temperature of about 33.5° C., results in rapid cell proliferation. When hFOB cells are cultured at an elevated temperature, i.e., at a temperature greater than about 37° C., preferably at about 38° C., cell proliferation slows considerably. Typically, proliferation does not occur at a restrictive temperature of 39.5° C. These results suggest that the conditional immortalization is dependant on a functional large T antigen. The resumption of rapid cell proliferation following conversion from the restrictive to the permissive temperatures is consistent with this hypothesis.

The differentiation of osteoblastic cells in culture involves a programmed developmental sequence. This sequence is characterized by an early proliferative stage during which osteoblastic cells are relatively undifferentiated, and later postconfluent stages which involve the expression of bone cell phenotypic markers and ultimately extracellular matrix mineralization. See, for example, M. A. Aronow et al., *J. Cell Physiol.*, 143, 213 (1989); and G. S. Stein et al., *FASEB J.*, 4, 3111 (1990).

There are numerous phenotypic markers and characteristics associated with osteoblast differentiation. These include: the expression of alkaline phosphatase (AP), osteopontin (OP), osteonectin (ON), osteocalcin (OC), bone sialoprotein (BSP), and type I collagen; an increase in cellular cAMP (cyclic adenosine menophosphate) levels in response to parathyroid hormone (PTH); an increase in OC levels in response to 1,25-(OH)$_2$D$_3$ treatment; and the formation of a mineralized matrix. hFOB cells express high levels of all of the above-mentioned osteoblast-associated proteins in post-confluent cultures. The expression of these phenotypic markers is indicative of stages of osteoblast differentiation which follow confluency in culture. Further, OC levels increase in response to 1,25-(OH)$_2$D$_3$ treatment, and cAMP levels increase in response to PTH treatment in postconfluent hFOB cells. These data suggest that hFOB cells contain functional vitamin D receptors and PTH receptors. In addition, hFOB cells form mineralized nodules in postconfluent cultures, which is characteristic of the late stages of osteoblast differentiation in culture. Therefore, hFOB cells appear to be relatively undifferentiated cells programmed to differentiate upon reaching confluence into cells which possess the full spectrum of osteoblast-associated features.

The conditional nature under which the hFOB cells of the present invention are immortalized prompted further investigation into the effect of cell proliferation on the expression of genes associated with osteoblast differentiation. Both alkaline phosphatase and 1,25-(OH)$_2$D$_3$-induced osteocalcin expression in postconfluent hFOB cells are significantly affected by incubation temperature. Since the incubation of hFOB cells at a restrictive temperature of about 39.5° C. results in the inactivation of the temperature sensitive SV40 T Ag and a subsequent decrease in cell proliferation, the effect on AP and OC gene expression suggests that changes in T antigen activity and subsequent effects on cell proliferation affect cell differentiation. See Table 1 for a summary of hFOB characteristics. It is possible that AP and OC expression are regulated by nuclear factors such as FOS and JUN, which are associated with cell proliferation. However, it is also possible that retinoblastoma may directly affect OC and AP gene expression, since the inactivation of SV40 large T Ag would affect Rb activity. However, the invention is not limited by any particular mechanistic theory of action.

TABLE 1

Effects of Temperature and Cell Density on hFOB Cell Functions

| A. | Temperature | 33° C. | 39° C. |
|---|---|---|---|
| | Proliferation | ++ | − |
| | AP | + | ++ |
| | 1,25 D$_3$ action on OC gene | + | +++ |
| | 1,25 D$_3$ action on AP gene | + | + |
| | E$_2$ action on c-fos gene | − | ++ |
| | TGF-β action on c-fos, Jun B | − | + |

| B. | Cell Density | Subconfluent | Confluent |
|---|---|---|---|
| | Proliferation | ++ | ± |
| | AP | + | ++ |
| | Mineralization/nodule formation | − | ++ |
| | Matrix production | − | ++ |

As stated above, the cells of the present invention can be used in cell culture studies of osteoblastic cell sensitivity to various agents, such as hormones, cytokines, and growth factors, or in tissue therapy. For example, they can be used in testing drugs by adding a drug to a culture of cells of the present invention at various incubation temperatures. In this way the drug's effect on different osteoblastic phenotypes can be investigated.

Specifically, the cells of the present invention can be stably transfected with, among other medically important genes, the gene for human wild-type estrogen receptor (hER), utilizing the cloning techniques described below. This makes them especially advantageous for use in medical research and treatment. Since untransfected hFOB 1.19 cells express very low levels of ER (less than about 200 activated receptors per nucleus), this invention is also directed toward the construction of subclones of hFOB 1.19 which are stably transfected with an ER expression vector. These estrogen-responsive human fetal osteoblastic subclones are referred to herein as hFOB/ER subclones. hFOB/ER stable transfectants express estrogen receptor at a level greater than about 400 activated receptors per nucleus, and preferably greater than about 800 activated receptors per nucleus. It is possible that these cells express greater than about 10,000 activated receptors per nucleus. They are responsive to treatment with 17β-estradiol. 17β-estradiol ($E_2$) is a clinically important estrogen, and the term estrogen-responsive means responsive to treatment with $E_2$. Generally, when the term estrogen is used, it refers to 17β-estradiol, although other estrogens may elicit similar responses. These responses, which are expected in estrogen target cells, include increases in endogenous progesterone receptor levels and c-fos steady state mRNA levels following $E_2$ treatment of hFOB/ER cells. The stably transfected hFOB/ER cells are extremely useful for studies of estrogen effects on osteoblast gene expression and physiology, and hence in the diagnosis and treatment of osteoporosis. For example, hFOB/ER cells that express moderate levels of the estrogen receptor (e.g., about 400 to about 3,000 activated receptors per nucleus) can be advantageously used as a model system to study the physiological effects of various drugs on osteoblast function since cultured human bone cells are known to express about 1600±400 activated receptor molecules per nucleus (E. F. Ericksen et al., *Science*, 241, 84–85 (1988)). Cells that express higher levels of ER (e.g., greater than about 3000) can also be advantageously used to investigate osteoblast function and gene response, and are more conveniently amenable to molecular biology experiments.

The cells of the present invention can also be used in a method of treating bone loss, e.g., resulting from osteoporosis, a fracture or break, and/or bone loss around the site of a surgical implant. This method involves placing immortalized human fetal osteoblastic cells which express a temperature sensitive mutant of simian virus 40 large T antigen into or onto a deteriorated bone at the point of deterioration. Specific methods and techniques used in such a tissue therapy regime are generally described by R. Langer et al., *Science*, 260, 920 (1993), which is incorporated herein by reference.

Cloning, Transfection, Transformation and Expression of Vector DNA in Immortalized hFOB Cells The conditionally immortalized cells of the present invention are constructed using standard molecular biology techniques that include the use of replicable expression vectors (described below) to express genes of interest in the host cell. Construction of suitable vectors employs standard ligation techniques known in the art. Isolated plasmids or DNA fragments are cleaved, tailored, and relegated in the form desired to generate the plasmids required.

Plasmids are transfected into host cells, preferably human fetal bone cells or the resultant conditionally immortalized hFOB cells of the present invention. Transfection refers to the taking up of an expression vector by a host cell. Many methods of transfection are known to one of ordinary skill in the art, e.g., calcium phosphate treatment, nuclear injection, protoplast fusion, or electroporation. Preferably, electroporation is used. Successful transfection is generally recognized when any indication of the operation of this vector occurs within the host cell. Successful transformation occurs when the DNA so introduced into the cell is replicable, either as an extrachromosomal element or by chromosomal integrant. Host cells are transfected and preferably transformed with the expression vectors of this invention and cultured in conventional nutrient media modified as appropriate for inducing promoters, selecting transformants, or expressing the genes encoding the desired sequences.

The human host cells used to produce the gene product of interest may be cultured in a variety of commercially available media. Preferably Delbecco's modified Eagles medium Ham F12 (DMEM/F12) (Sigma Chemical Co., St. Louis, Mo.) is used. In addition, any suitable custom-prepared media such as that described in, e.g., Ham et al., *Methods Enzymol.*, 58, 44 (1979) or Barnes et al., *Anal. Biochem.*, 102, 255 (1980), may be used as culture media for the host cells. Any of these media may be supplemented as necessary with hormones and/or other growth factors (such as insulin, transferrin, or epidermal growth factor), salts (such as sodium, calcium, or magnesium chloride or phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Plasmids from the transformants are isolated, analyzed by restriction endonuclease digestion, and/or sequenced by methods known in the art. See, e.g., J. Messing et al., *Nucl. Acids Res.*, 9, 309 (1981) and Maxam et al., *Methods Enzymol.*, 65, 499 (1980).

Construction of Replicable Expression Vectors

Nucleic acid (e.g., cDNA or genomic DNA) comprising the gene of interest is inserted into a replicable vector, preferably a circular or linearized plasmid vector, for expression of the gene product. Preferably, DNA encoding a gene product that confers immortality, more preferably conditional immortality, on the host cell is inserted into the expression vector. Most preferably, this DNA encodes a temperance sensitive SV40 large T antigen. In addition thereto, other expression vectors containing DNA encoding proteins, e.g., growth factors and hormones, preferably the human estrogen receptor, can be constructed and used to alter the cell phenotype. Further, additional expression vectors containing genes conferring antibiotic resistance, such as neomycin resistance, or other marker genes may preferably be used in the same host cell.

Many expression vectors are available, and selection of the appropriate vector depends on the size of the nucleic acid to be inserted into the vector and the host cell to be transformed with the vector. Most expression vectors are "shuttle" vectors, i.e., they are capable of replication in at least one class of organism but can be transfected into another organism for expression. For example, a vector is cloned in *E. coli* and then the same vector is transfected into yeast or mammalian cells for expression even though it is not capable of replicating independently of the host cell chromosome.

Replicable expression vector components generally include, but are not limited to, one or more of the following: a signal sequence, an origin of replication, one or more marker genes, an enhancer element, a promoter and a transcription termination sequence. In mammalian cell expression, a native signal sequence may be satisfactory, although other mammalian signal sequences may be suitable, such as signal sequences from secreted polypeptides of the same or related species, as well as viral secretory leaders, for example, the herpes simplex gD signal. Generally, the origin of replication component is not needed for mammalian expression vectors, although the SV40 origin is typically used because it contains the early promoter (see below).

The selection or marker gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin, mycophenolic acid, or preferably, hygromycin. These three examples employ bacterial genes under eukaryotic control to convey resistance to the appropriate drug G418 or neomycin (geneticin), xgpt (mycophenolic acid,) or hygromycin, respectively.

Expression vectors usually contain a promoter that is recognized by the host organism and is operably linked to the gene of interest. Promoters are untranslated sequences located upstream (5') to the start codon of a structural gene (generally within about 100 to 1000 bp) that control the transcription and translation of a particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known in the art. These promoters are operably linked to the gene of interest by removing the promoter from the source DNA by restriction enzyme digestion and inserting the isolated promoter sequence into the vector. Both the native promoter sequence and many heterologous promoters may be used to direct amplification and/or expression of the gene of interest. Heterologous promoters are preferred, as they generally permit greater transcription and higher yields of expressed protein as compared to the native promoter. Numerous promoter sequences are known for eukaryotes. Virtually all eukaryotic genes have an AT-rich region located approximately 25 to 30 bases upstream from the site where transcription is initiated Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. Any of these sequences is suitably inserted into eukaryotic expression vectors. Transcription from vectors in mammalian host cells is controlled, for example, by promoters obtained from the genomes of viruses such as polyoma virus, fowlpox virus, adenovirus (such as Adenovirus 2) bovine papilloma virus, avian sarcoma virus, Simian Virus 40 (SV40), hepatitis-B virus and, preferably, cytomegaiovirus; from heterologous mammalian promoters, e.g., the actin promoter or an immunoglobulin promoter; from heat-shock promoters; and from the promoter normally associated with the gene of interest, provided such promoters are compatible with the host cell systems. The early and late promoters of the SV40 are conveniently obtained as an SV40 restriction fragment that also contains the SV40 viral origin of replication. Fiers et al., *Nature*, 273, 113 (1978); Mulligan et al., *Science*, 209, 1422–1427 (1980); Pavlakis et al., *Proc. Natl. Acad. Sci. USA*, 78, 7398–7402 (1981). The immediate early promoter of the human cytomegalovirus is conveniently obtained as a HindIII E restriction fragment. Greenaway et al., *Gene*, 18, 355–360 (1982).

Transcription of the gene of interest by higher eukaryotes is often increased by inserting an enhancer sequence into the vector. Enhancers are cis-acting elements of DNA, usually about 10–300 bases long, that act on a promoter to increase its transcription. Enhancers are relatively orientation- and position-independent, having been found 5' to the transcription unit, within an intron as well as within the coding sequence itself. Many enhancer sequences are now known from mammalian genes (globin, elastase, albumin, alpha-fetoprotein, and insulin). Typically, however, an enhancer from a eukaryotic cell virus is used. Examples include the SV40 enhancer on the late side of the replication origin (bp 100–270), the cytomegalovirus early promoter enhancer, the polyoma enhancer on the late side of the replication origin, and adenovirus enhancers. The enhancer may be spliced into the vector at a position 5' or 3' to the gene being transfected, but is preferably located at a site 5' of the promoter.

Expression vectors used in eukaryotic host cells will also contain sequences necessary for the termination of transcription and for stabilizing the transcribed mRNA. Such sequences are commonly available from the 5' and, occasionally, 3' untranslated regions of eukaryotic or viral DNAs or cDNAs. These regions contain nucleotide segments transcribed as polyadenylated fragments in the untranslated portion of mRNA. Preferably, the SV40 polyadenylation signal is used.

The invention has been described with reference to various specific and preferred embodiments and will be further described by reference to the following detailed examples. It is understood, however, that there are many extensions, variations, and modifications on the basic theme of the present invention beyond that shown in the examples and detailed description, which are within the spirit and scope of the present invention.

EXPERIMENTAL EXAMPLES

Example I.

Construction and Characterization of hFOB 1.19 Cells

A. Materials Used

Delbecco's modified Eagles medium Ham F12 (DMEM/F12 1:1 w/w) mix, menadione (vitamin $K_3$), ascorbic acid (vitamin C), human parathyroid hormone fragment 1–34 (PTH 1–34), prostaglandin type $E_2$ ($PGE_2$ 11,15-dihydroxy-9-oxoprosta-5,13-dien-1-oic acid), forskolin (7β-acetoxy-1α,6β,9α-trihydroxy-8,13-epoxy-labd-14-en-11-one), 10× trypsin-EDTA and the alkaline phosphatase enzyme assay kit were purchased from Sigma Chemical Co. (St. Louis, Mo.). Fetal Bovine Serum (FBS) was purchased from Flow Laboratories Inc. (McLean, Va.) and 1,25-dihydroxy vitamin $D_3$ (1,25-$(OH)_2D_3$) was purchased from Biomol (Plymouth Meeting, Pa.). Neomycin G418 (geneticin) was purchased from Gibco Laboratories (Gaithersburg, Md.) and electroporation cuvettes were purchased from Bio-Rad Laboratories (Hercules, Calif.). The substrate-based staining kit for alkaline phosphatase was purchased from Vector Laboratories Inc. (Burlingham, Calif.) and the human osteocalcin RIA kit was purchased from Immutopics (San Clemente, Calif.). The cAMP assay kit was purchased from Amersham Corp. (Arlington Heights, Ill.) and the peroxidase immunostaining kit was purchased from Biomeda Corp. (Foster City, Calif.). The SV40 T Ag-specific monoclonal antibody was purchased from Oncogene Science (Uniondale, N.Y.) and $^3$H-labelled thymidine was purchased from New England Nuclear Research Products, DuPont Company (Boston, Mass.). Polyclonal antibodies specific for human osteopontin (OP) LF-7, osteonectin (ON) LF-BON, osteocalcin (OC) LF-32, bone sialoprotein (BSP) LF-100, and type I collagen LF-67 were obtained from Dr. Larry W. Fisher at the Bone Research Branch, National Institute of Dental Research, National Institutes of Health, Bethesda, Md. 20892. See also, L. W. Fisher et al., *J. Biol. Chem.*, 262, 9702 (1987), which is incorporated herein by reference. The T Ag expression vector pUCSVtsA58 is available from D. Wynford-Thomas without restriction of use (Department of Pathology, CRC Thyroid Tumour Biology Research Group, University of Wales College of Medicine, Heath Park, Cardiff CF4 4XN, United Kingdom). See also D. Wynford-Thomas et al., *Mol. Cell. Biol.*, 10, 5365 (1990); P. Tegtmeyer, *J. Virology*, 15 613 (1975); and A. J. Ridley et al., *EMBO J.*, 7, 1635 (1988). The neomycin resistance expression vector pSV2neo was purchased from American Type Culture Collection (Rockville, Md.).

B. Methods Used

1. Isolation, Transfection and Screening of hFOB Cells

Limb tissue was obtained from a spontaneous miscarriage under institutionally approved protocols as a source for primary cultures. The limb tissue was placed in phosphate buffered saline and homogenized with scalpel blades, then digested with collagenase (0.5 mg/ml) for 30 minutes and trypsin (10 mg/ml) for 30 minutes. The cells were then seeded into 100 mm tissue culture plates containing phenol red-free DMEM/F12 media with 10% (v/v) FBS and 10% (v/v) human serum. The cells were incubated at 37° C. in 5% $CO_2$ humidified air and the media was replaced every 48 hours until sufficient numbers of cells were present for the transfection procedure. Cells which did not adhere to the culture plates were discarded. Adherent cells were removed from the culture plates with trypsin-EDTA treatment. Briefly, cells were rinsed with phosphate buffered saline (PBS). Then a 10× stock solution of trypsin-EDTA was diluted 10 fold with PBS and enough 1× solution was added to cover the surface of the culture plate and incubated at 37° C. until the adherent cells were released. The cells were then rinsed with serum-containing media and centrifuged (5 minutes at 900×g), then rinsed again with serum-free media and centrifuged (5 minutes at 900×g).

The pellet of cells (containing approximately $8\times10^6$) was resuspended in 0.4 ml of serum-free media containing 10 μg linearized T Ag expression vector pUCSVtsA58 and 2 μg linearized neomycin resistance expression vector pSV2neo (P. J. Southern et al., *J. Mol. Appl. Gen.*, 1 327 (1982)). The cell/DNA suspension was placed in an electroporation cuvette and incubated at 4° C. for 10 minutes. The cells were then subjected to a pulse of 900 V/cm at 960 μFD using a Biorad electroporation device and incubated at 4° C. for 10 minutes more following the pulse. The cells were then seeded into tissue culture plates containing DMEM/F12 media with 10% (v/v) FBS at 37° C. After 48 hours and every 48 hours thereafter, the media was replaced with fresh media containing 600 μg/ml neomycin G418. After 7–10 days of neomycin selection, resistant colonies were visible and were maintained in media containing 300 μg/ml neomycin G418. More than 50 neomycin resistant colonies were passaged by trypsin-EDTA treatment in glass cylinders and seeded into separate tissue culture wells for further growth and screening.

When sufficient numbers of cells from each colony were obtained, they were screened for alkaline phosphatase activity by a substrate-based staining technique, as recommended in the substrate-based staining kit for alkaline phosphatase purchased from Vector Laboratories Inc. Briefly, confluent cells were rinsed twice with PBS and fixed with absolute ethanol. Then alkaline buffer (100 mM Tris-HCl pH 9.5) containing substrate was added to the cells and incubated at 37° C. for 30 minutes. Five of the colonies which were screened had high levels of AP activity (were heavily stained). The highest activity was observed in the clone hFOB 1.19.

2. Thymidine Incorporation

The hFOB cells were seeded at low density ($5\times10^3$ cells/well, 48 well dish) in the DMEM/F12 media with 10% (v/v) FBS and cultured for 16–18 hours at 33.5° C. The cells were then cultured for 24 hours at the test temperature (33.5° C., 38.0° C., 39.5° C.), and then pulsed with 0.5 μCi of $^3$H-labelled thymidine for 24 hours for each day of the time course. After each thymidine pulse, the cells were rinsed three times with 10% (w/v) trichloroacetic acid, then solubilized in 0.2% (w/v) sodium hydroxide. The solute was then mixed with scintillation cocktail for quantitation of $^3$H in a Beckman model LS2800 scintillation counter.

3. Karyotype Analysis

Karyotype analysis was performed in the Mayo Cytogenetics Laboratory by the method described in J. L. Spurbeck et al., *Cancer Genet. Cytogenet.*, 32, 59 (1988), as detailed for fibroblast cultures, which is incorporated herein by reference. Briefly, hFOB cells were seeded at low density on glass coverslips in tissue culture dishes. At 10–30% confluence, the cells were treated with 0.25 μg/ml colcemid for 30–60 minutes. The cells were then prepared for metaphase spreads using a Tecan model 505 robotic sample processor.

4. Immunocytochemistry

Immunostaining for SV40 T Ag was performed by fixing subconfluent hFOB cells with 100% methanol for 10 minutes at 4° C., then blocking in 1% bovine serum albumin (BSA) in PBS for 60 minutes. Primary antibody (in 1% BSA in PBS) was added and incubated on the cells at 25° C. for 60 minutes. The cells were rinsed with PBS and a secondary antibody (goat anti-mouse IgG) was added to the cells and incubated for 30 minutes at 25° C. Then peroxidase reagent and chromogen reagent were added according to the manufacturers specifications. Immunostaining for OP, OC, ON, BSP, and type I collagen were performed in the same manner except that day 8 (postconfluent) cells were fixed in absolute ethanol, blocking was done with 10% (v/v) FBS in PBS, and the secondary antibody was goat anti-rabbit IgG.

5. cAMP Quantitation

The hFOB cells were cultured in 6 well dishes to confluence (approximately $5\times10^5$ cells/well) at 33.5° C. in DMEM/F12 media with 10% (v/v) FBS, then the culture media was replaced and the cells were incubated at 39.5° C. for 48 hours. The cells were pretreated with 1 mM isobutylmethylxanthene (IMBX) for 2 minutes. The cells were then treated with either 1–34 PTH (1–100 nM), $PGE_2$ or forskolin (10 μM) for 10 minutes. The media were removed from the cells and the cells were rinsed immediately with cold (4° C.) PBS, scraped from the tissue culture dish in cold (−20° C.) 70% (v/v) ethanol, transferred to 1.5 ml microcentrifuge tubes, and sonicated on ice. The cell lysate was lyophilized in a speed vac concentrator and redissolved in 0.25 ml of Tris-EDTA buffer (50 mM Tris, pH 7.5, 4 mM EDTA). A portion (20–50 μl) of each lysate was mixed with 50 μl $^3$H-cAMP and 100 μl cAMP-binding protein solution and incubated at 4° C. for 120 minutes. The binding reaction was then mixed with 100 μl activated dextran-coated charcoal and centrifuged at 12,000×g for 5 minutes. A portion (200 μl) of the supernatant was then mixed with scintillation cocktail for quantitation of $^3H$.

6. Staining of Mineralized Matrix

Postconfluent hFOB cells were fixed in 1% (w/v) paraformaldehyde in Tris buffered saline (TBS=20 mM Tris, pH 7.4, 0.15M NaCl) and rinsed with TBS. The cells were then stained by the yon Kossa procedure as modified by R. K. Schenk et al. in *Methods of Calcified Tissue Preparation;* G. R. Dickson, Eds.; Elsevier; 1–4 (1984), which is incorporated herein by reference. Briefly, the cells were treated with 5% (w/v) silver nitrate in the dark for 15 minutes. The cells were then rinsed with distilled water, subjected to ultraviolet light for 5 minutes, treated with sodium carbonate/formaldehyde solution for 2 minutes, and finally treated with Farmer's reducer as described for 30 seconds.

7. Alkaline Phosphatase and Osteocalcin Assays

The hFOB cells were cultured in 6 well dishes to confluence in DMEM/F12 media with 10% (v/v) FBS at 33.5° C., then rinsed with about 3 ml serum-free media twice. The media was replaced with differentiation media (DMEM/F12 with 0.2% (v/v) charcoal-stripped FBS (csFBS), 100 μl ascorbic acid, and $10^{-8}$ menadione) and the cells were incubated at the desired temperature for 24 hours. The media was replaced again with differentiation media and the cells were treated with various doses of 1,25-$(OH)_2D_3$ or ethanol vehicle for 48 hours. The media was removed and utilized for osteocalcin assays while the AP reaction was initiated by rinsing the cells twice with PBS and adding 0.5 ml of alkaline lysis buffer (0.75M 2-Amino-2-methyl-1-propanol, pH 10.3) containing p-nitrophenol phosphate substrate (2 mg/ml), and incubating at 37° C. for 30 minutes. The reaction solution was mixed with an equal volume of 50 mM NaOH, then diluted 1:40 with 20 mM NaOH. The absorbance at 410 nm was determined and compared to p-nitrophenol standards. A portion of the reaction solution was used to determine total protein concentration by the Bradford method, as disclosed by M. M. Bradford, *Anal. Biochem.*, 72, 248 (1976), which is incorporated herein by reference.

A portion of conditioned media (400 μl) or media plus known OC standards (provided in kit) were mixed with a $^{125}I$-labelled antibody to human osteocalcin (anti-OC) and a plastic bead coated with the anti-OC antibody. These mixtures were incubated 18–24 hours at 25° C., then the beads were rinsed with wash buffer as specified by the manufacturer in the osteocalcin RIA kit purchased from Immutopics. Briefly, the binding reaction buffer was removed and washed three times with 2 ml each time of a wash buffer. The rinsed beads were put into scintillation cocktail for quantitation of $^{125}I$. The control and treated samples were compared to the standard curve for quantitation of OC.

C. Results

1. Isolation, Transfection and Screening of hFOB Cells

Primary cultures isolated from fetal tissue were transfected with a gene coding for a temperature sensitive mutant (tsA58) of SV40 large T antigen, along with a gene coding for neomycin (G418) resistance. Individual neomycin resistant colonies were screened for alkaline phosphatase (AP) specific staining. The clone with the highest AP level, hFOB 1.19, was examined further for other osteoblast phenotypic markers. Thymidine incorporation experiments indicated that incubation of hFOB 1.19 cells at a permissive temperature of 33.5° C. resulted in rapid cell division, whereas little or no cell division occurred at a restrictive temperature of 39.5° C. Measurement of AP activity in hFOB cell extracts indicated that cells cultured at 39.5° C. had 2–3 fold higher levels of AP than cells cultured at 33.5° C. Further, AP activity increased in a dose-dependant manner following treatment with 1,25-Dihydroxyvitamin $D_3$ (1,25-$(OH)_2D_3$) when cultured at either temperature. Similarly, radioimmunoassay (RIA) analyses showed that the level of osteocalcin secreted from 1,25-$(OH)_2D_3$-treated hFOB 1.19 cells was 10 fold higher when the cells were cultured at 39.5° C. compared to cells cultured at 33.5° C. In addition, osteocalcin levels in hFOB 1.19-conditioned media increased in a dose-dependant manner following 1,25-$(OH)_2D_3$ treatment at both 39.5° C. and 33.5° C. incubations. Treatment of hFOB 1.19 cells with 1–34 parathyroid hormone (PTH) at 39.5° C. resulted in a 3 fold increase in cAMP levels as measured by RIA. Upon reaching confluence, hFOB 1.19 cultures went through programmed differentiation and formed mineralized nodules as observed by von Kossa staining. Further, immunostaining of postconfluent, differentiated hFOB cells showed that high levels of osteocalcin, osteopontin, osteonectin, bone sialoprotein, and type I collagen were expressed.

2. Temperature Control of hFOB Cell Proliferation

Since hFOB 1.19 cells were transfected with a temperature sensitive mutant tsA58 of SV40 large T antigen, the effect of incubation temperature on hFOB 1.19 cell proliferation was examined. The rate of thymidine incorporation by hFOB 1.19 cells cultured at various temperatures was measured to indirectly reflect the rate of hFOB 1.19 cell division. These data (FIG. 1) indicate hFOB cells cultured at the permissive temperature of 33.5° C. proliferated rapidly with a doubling time of about 36 hours. Similarly, microscopic inspection indicated an increase in cell number from less than about 20% confluence to greater than about 80% confluence during the time course. In contrast, hFOB 1.19 cells cultured at the restrictive temperature of 39.5° C. did not appear to proliferate during the four day time course, whereas cells cultured at 38.0° C. proliferated very slowly, with a doubling time of greater than 96 hours. However, when the cells were switched back to 33.5° C. after 24 hours at 39.5° C., proliferation resumed and attained a rate similar to that observed with cells grown continuously at 33.5° C.

3. Karyotype Analysis

In order to characterize the chromosomal makeup of the hFOB 1.19 cells, karyotype analysis was performed on passage 12 cells. The data from 100 metaphases indicate that 43% of the cells were diploid and 57% were tetraploid. Among a group of 12 diploid metaphases analyzed further, 7 were normal 46,XX and 5 were 44–46,XX with an 18q+ translocation. Chromosome polymorphism patterns were consistent with a clonal cell population. The hFOB 1.19 clone has been cultured at 33.5° C. up to passage 30 (approximately 100 population doublings) without crisis. At passage 32 to 34 the cells entered crisis and proliferation slowed considerably.

4. Expression of Osteoblast Phenotypic Markers and SV40 T Antigen

To determine whether hFOB 1.19 cells express proteins which are characteristic of the osteoblast phenotype and to confirm that the transfected SV40 large T antigen (T Ag) gene is expressed, immunostaining was performed with antibodies specific to osteopontin (OP), osteonectin (ON), osteocalcin (OC), bone sialoprotein (BSP), type I collagen, and T Ag. The results of these immunostaining experiments (FIG. 2) showed that high levels of the differentiation markers OP, ON, OC, BSP, and type I collagen were expressed in postconfluent hFOB cells cultured at 33.5° C. In addition, high levels of T Ag were localized in the nuclei of hFOB cells.

5. Induction of cAMP Levels by PTH and $PGE_2$

Figure 3:
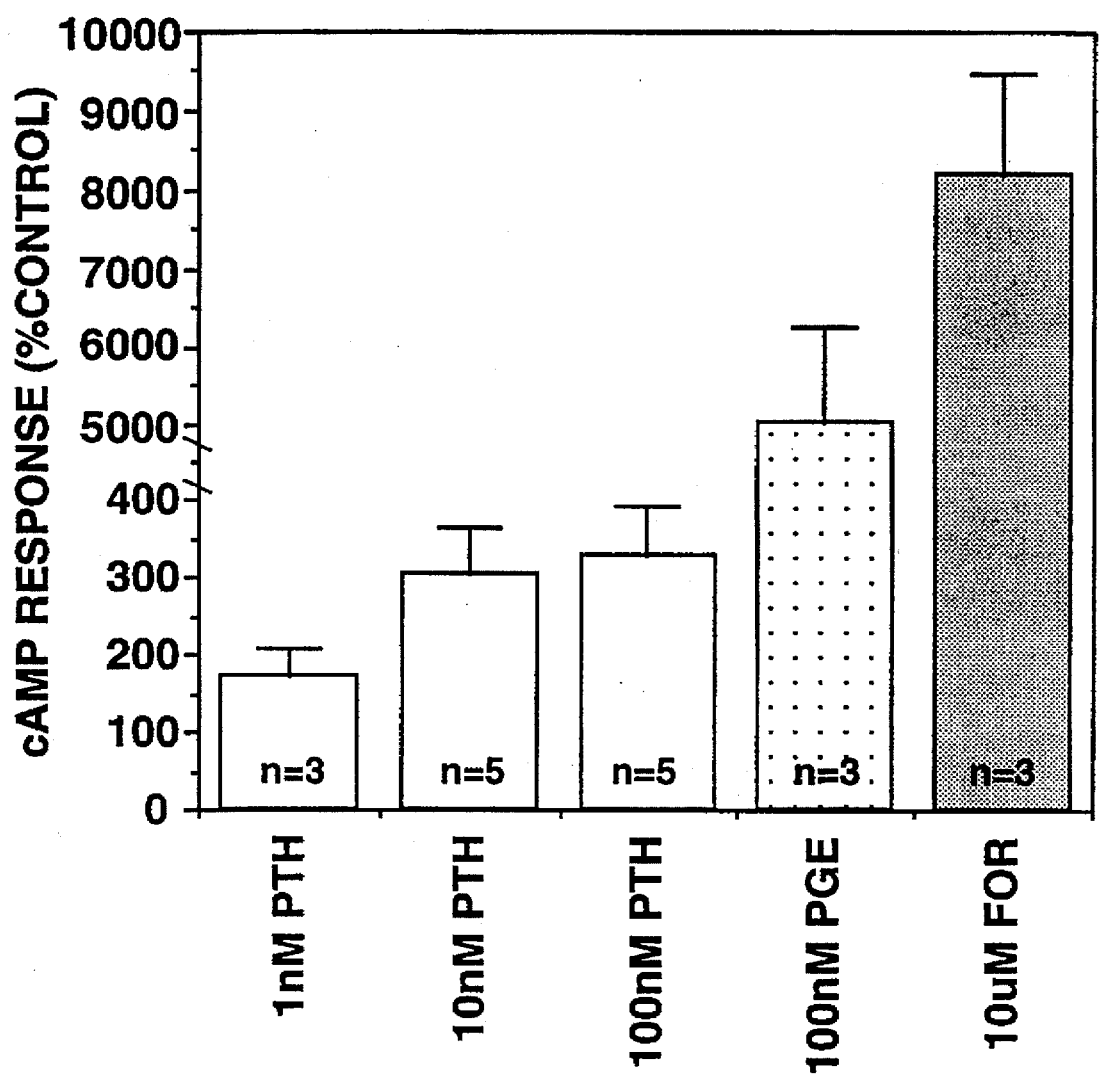
FIG. 3. Induction of cAMP levels in hFOB 1.19 cells by various agonists. Confluent hFOB 1.19 cells (at 39.5° C.) were pretreated with 1 mM isobutylmethylxanthene (IBMX) for 2 minutes, then treated with the indicated dose of each agonist for 10 minutes. Quantitation of cAMP levels was then performed by radioimmune assay (RIA), and the amount of cAMP (pmoles/$10^5$ cells) for each agonist treatment was compared to control treatment (IBMX only) and expressed as a percentage (as denoted). Error bars=SEM (standard error of the mean), n=number of experiments (as denoted).
Figure 4A:
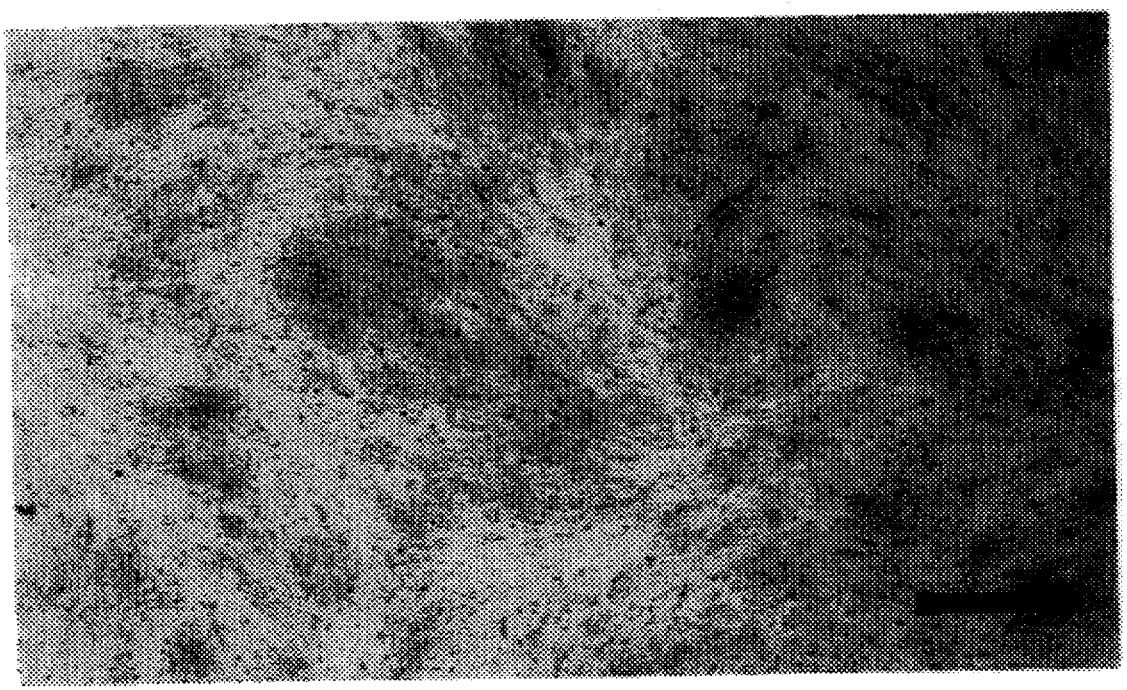
FIGS. 4A–4E. Mineralization of the extracellular matrix by hFOB 1.19 cells. The hFOB cells were cultured at 33.5° C. past confluence (day 0), then stained by the modified yon Kossa (Schenk et al., in *Methods of Calcified Tissue Preparation;* G. R. Dickson et al., Eds.; Elsevier; 1–4 (1984)) method to visualize mineralization of the extracellular matrix on the following days: (A) day 2; (B) day 4; (C) day 6; (D) day 8; and (E) day 10. Darkly stained areas are nodules with mineralized matrix (25× magnification).
Figure 4B:
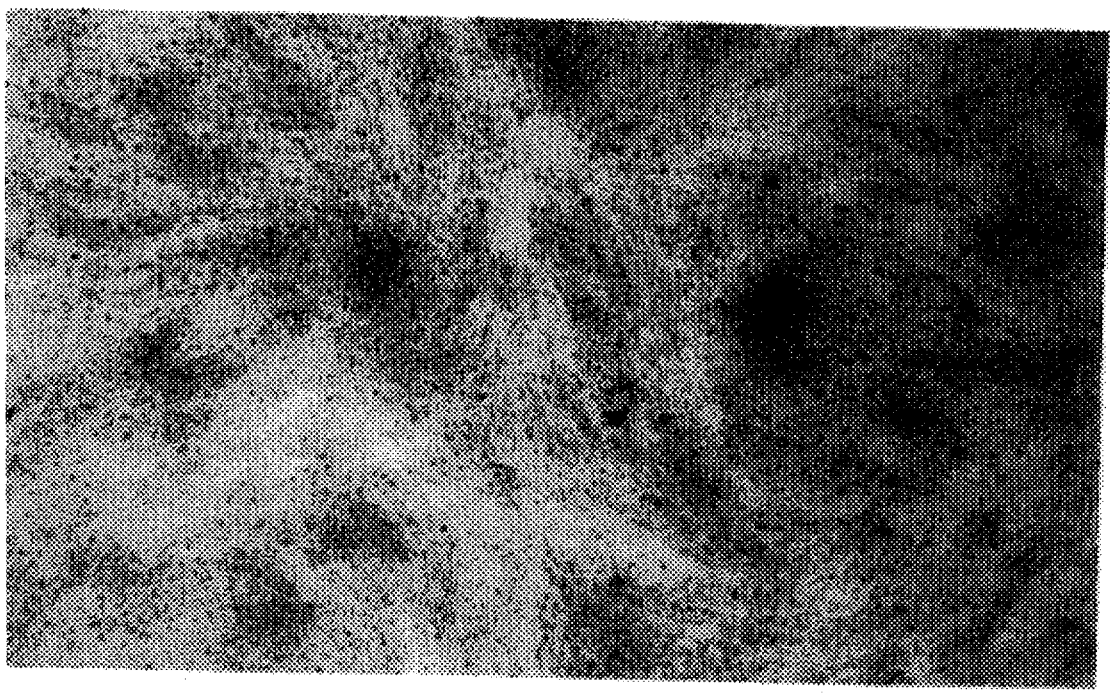
Figure 4C:
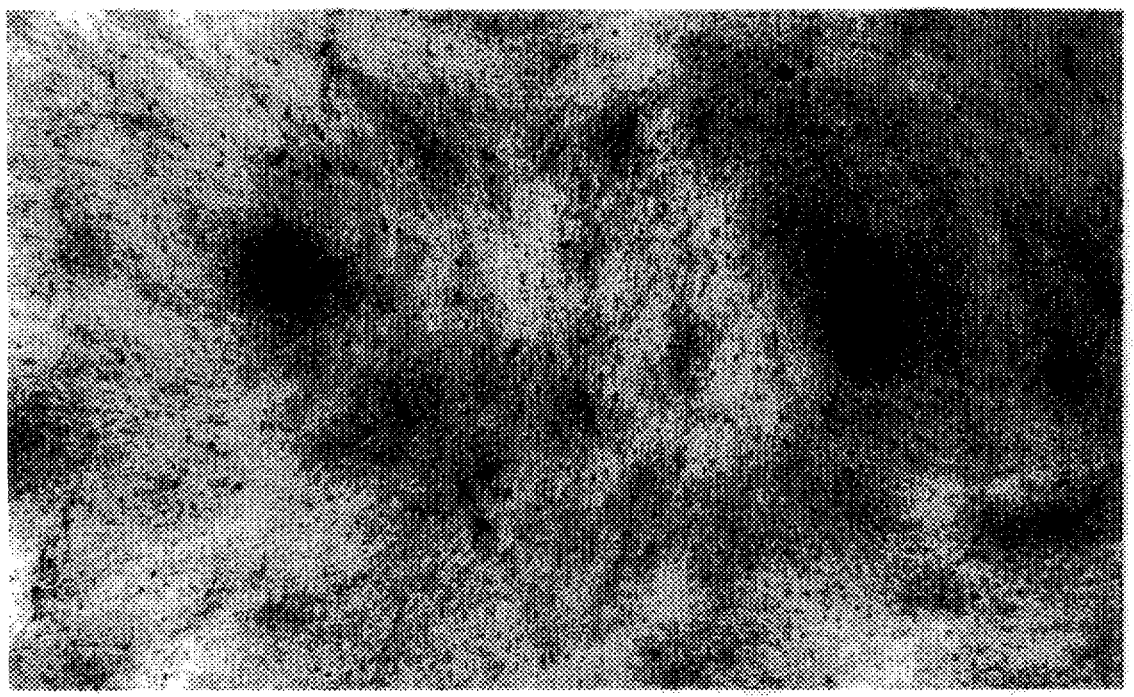
Figure 4D:
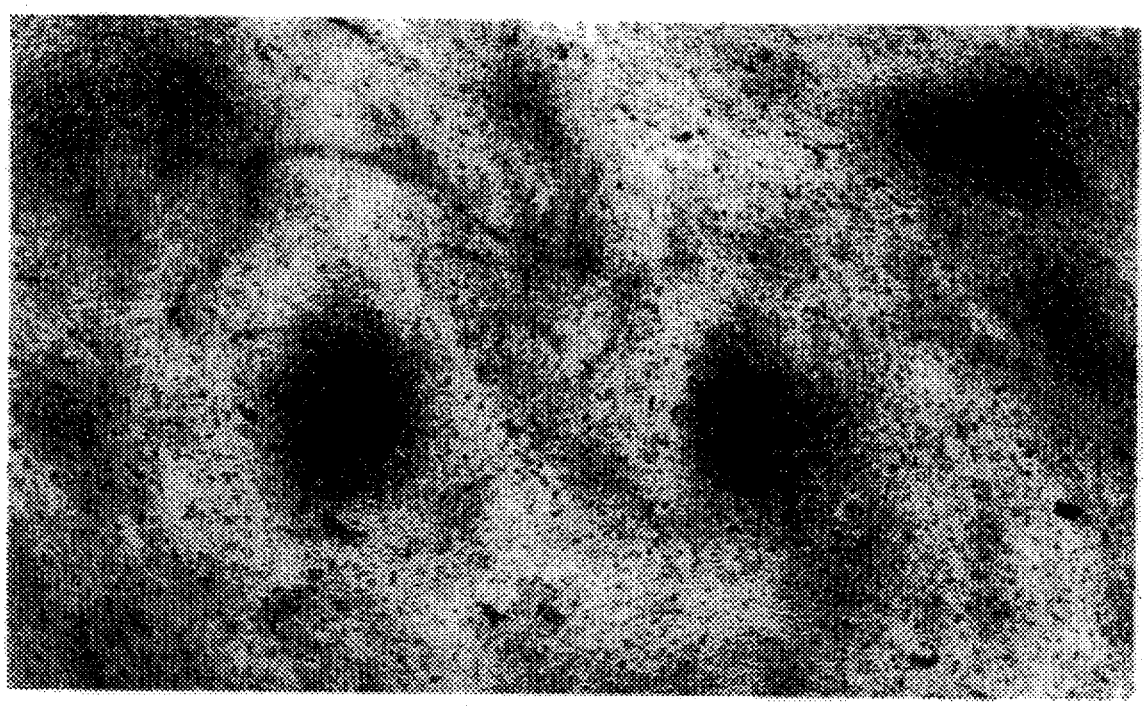
Figure 4E:
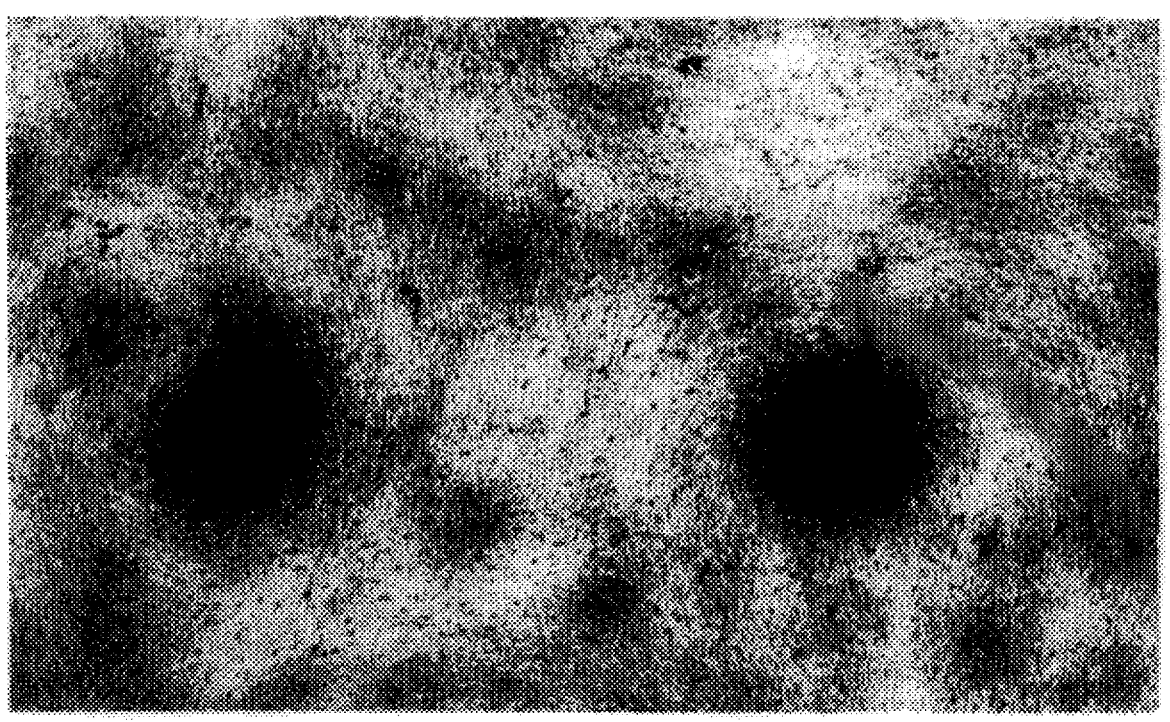
Figure 5A:
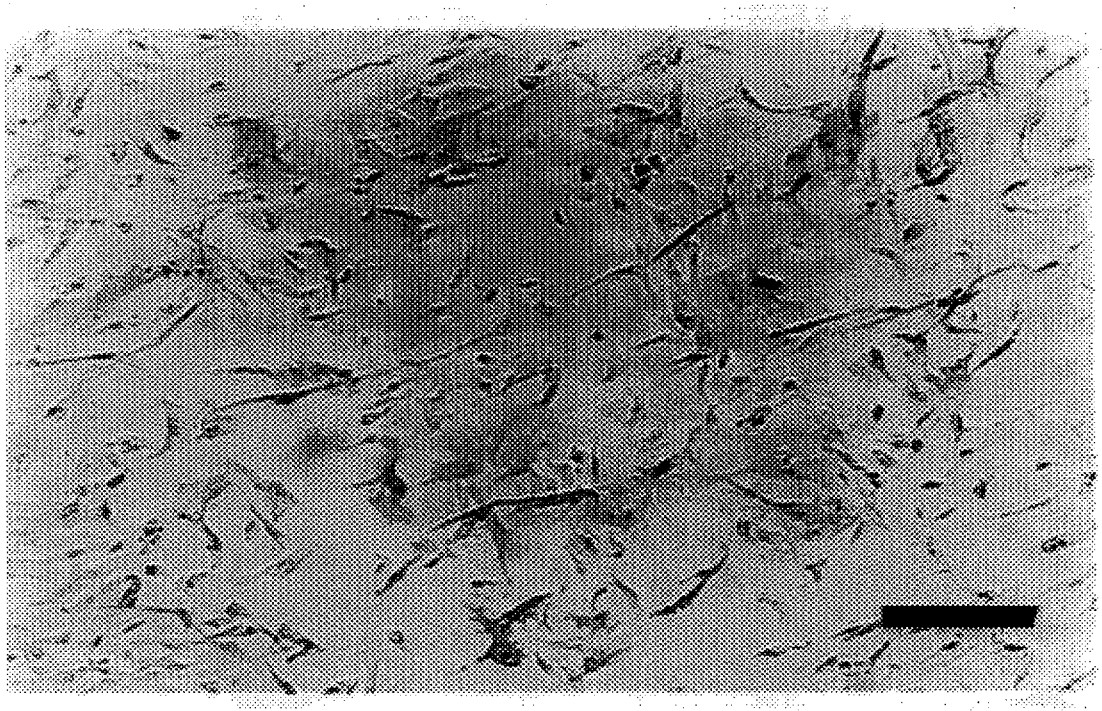
FIGS. 5A–5E. Regulation of alkaline phosphatase (AP) activity in hFOB 1.19 cells. Subconfluent (A and C) or confluent (B and D) hFOB cells were incubated at either 33.5° C. (A and B) or 39.5° C. (C and D) in differentiation media, then fixed and incubated with a substrate-based stain for AP activity in situ. Dark staining indicates high AP activity (200× magnification). (E) Confluent hFOB cells were incubated at the indicated temperatures in differentiation media (DMEM/F12 with 0.2% (v/v) charcoal-stripped FBS (csFBS), 100 µg/ml ascorbic acid, and $10^{-8}$ menadione) for 24 hours, then treated for 48 hours with the indicated doses of 1,25-dihydroxy vitamin $D_3$ (1,25-$(OH)_2D_3$), or ethanol vehicle (control) at the indicated temperatures. AP activity in cell extracts was then measured using the p-nitrophenol phosphate assay and normalized to total protein. Units=µmoles p-nitrophenol/hour at 37° C. Error bars=1 standard deviation, n=6 experiments. **=P<0.01 vs control, $=P<0.001 39.5° C. vs 33.5° C., two-tailed student's paired T test.
Figure 5B:
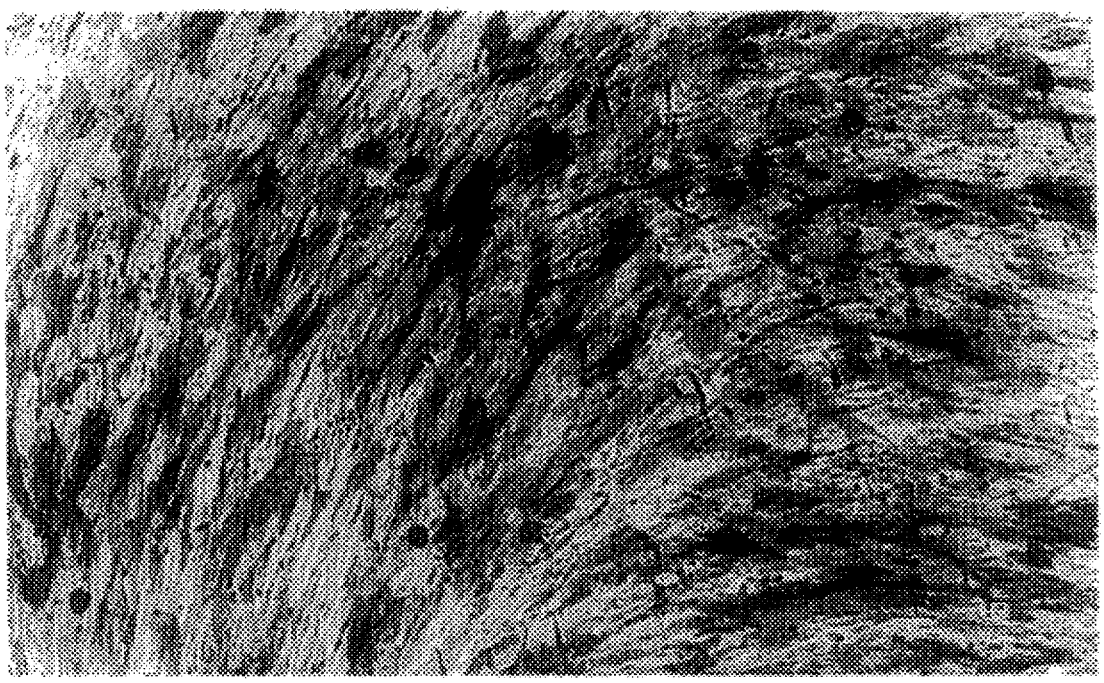
Figure 5C:
Figure 5D:
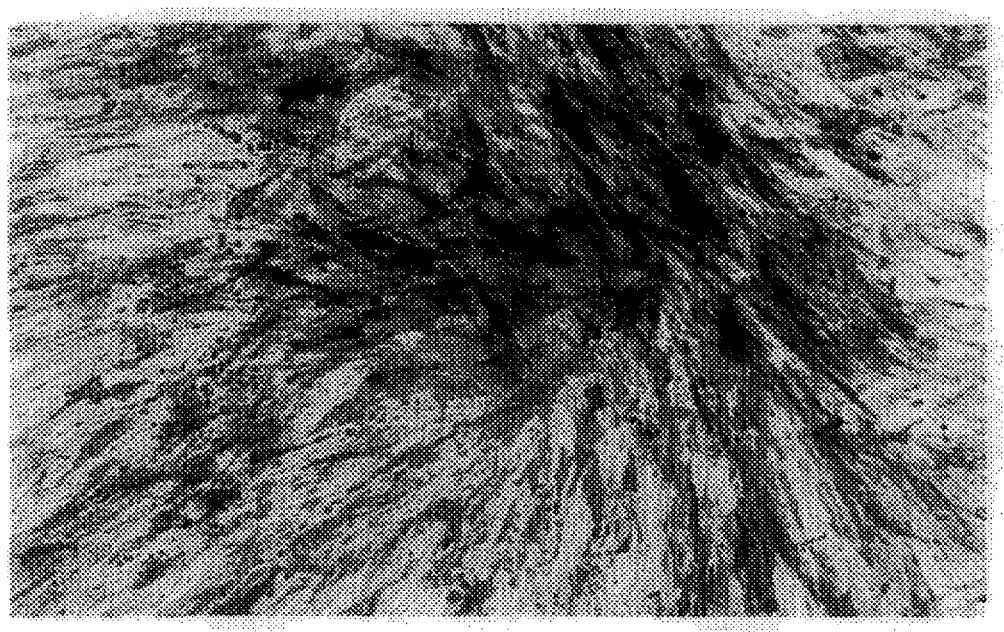
Figure 5E:
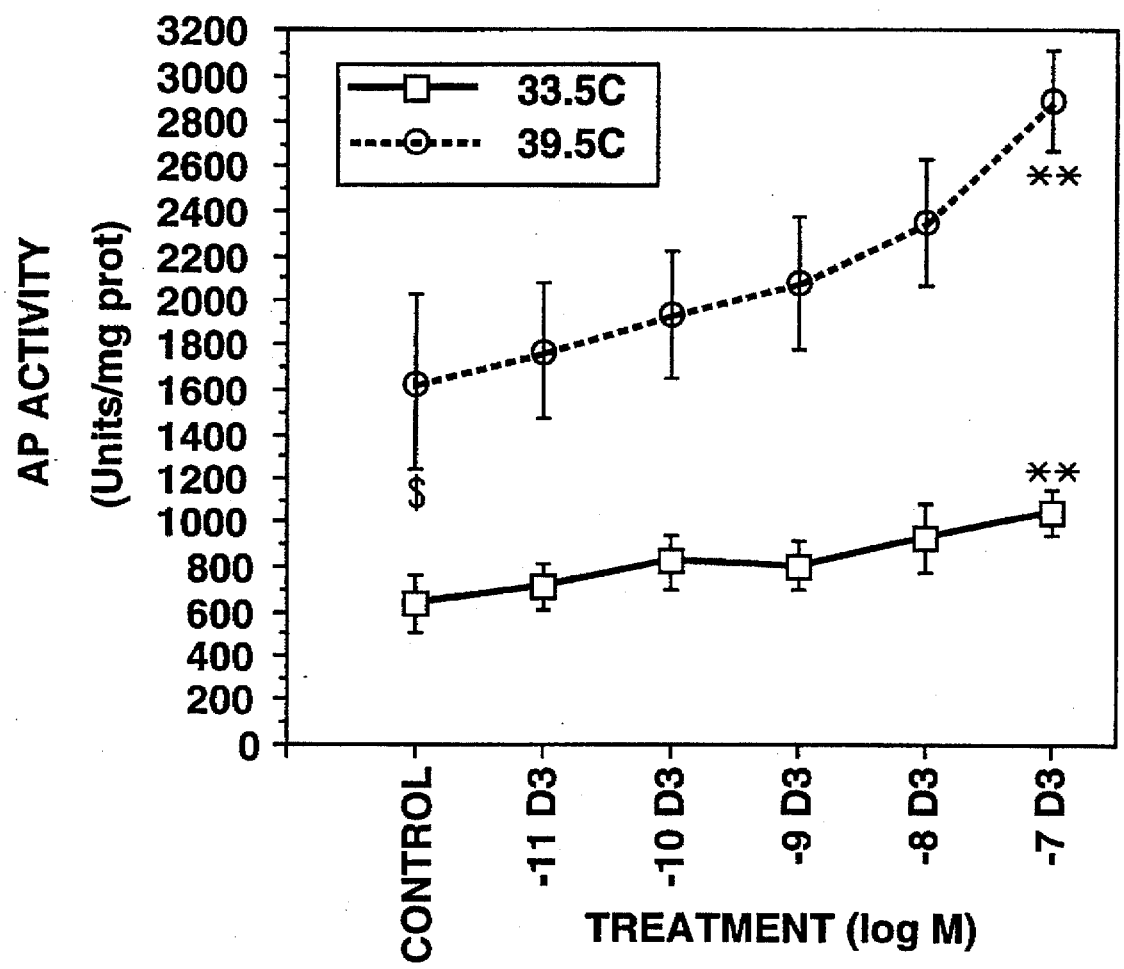

Since cAMP levels have been shown previously to be affected by PTH and $PGE_2$ in other osteoblastic cell lines, these cAMP agonists were examined for their activity in hFOB 1.19 cells by radioimmunoassay. The data (FIG. 3) indicate that cAMP levels increased more than 3 fold when hFOB 1.19 cells were treated with 10 nM or 100 nM PTH, but increased less than 2 fold when treated with 1 nM PTH. Dramatic increases in cAMP levels were observed following treatment with 100 nM $PGE_2$ (>50 fold increase) or with the known agonist 10 μM forskolin (>80 fold increase).

6. Formation of Mineralized Nodules

Many osteoblastic cell lines have been shown to form mineralized nodules during the processes of cell differentiation and matrix mineralization. Upon culturing hFOB 1.19 cells beyond confluency (day 0) at 33.5° C., formation of mineralized nodules occurred gradually until nodules were clearly visible by day 8–10. Nodule formation was also observed in postconfluent cells cultured at 39.5° C. To visualize calcium deposition within the nodules, the cells were stained by the von Kossa procedure and examined under light microscopy. These data (FIG. 4) showed that calcium deposition within the nodules was easily detectable by day 4–6 and became extensive by day 8–10 post confluency. Interestingly, nodule formation and calcium deposition were extensive even without the addition of glycerophosphate or high doses of glucocorticoids to the culture media.

7. Regulation of Alkaline Phosphatase Activity

Since initial screenings of neomycin-resistant transfectants indicated that the highest level of AP was present in hFOB 1.19 cells, the regulation of AP in this clone was examined by performing substrate-based staining and standard enzyme assays under various culturing conditions. To determine whether AP activity within hFOB 1.19 cells changes upon reaching confluency or changes by incubation temperature, substrate-based staining was performed. These data (FIG. 5, panels A–D).indicated that AP activity increased dramatically upon reaching confluency at either incubation temperature (33.5° C. or 39.5° C.). This reflects a change in the differentiation state of hFOB 1.19 cells to a more mature phenotype. The mount of AP-specific staining was deafly much higher in confluent cells (FIG. 5, panels B and D) than subconfluent cells (FIG. 5, panels A and C). Although there appeared to be a slightly higher level of AP activity in hFOB 1.19 cells cultured at 39.5° C. (FIG. 5, panels C and D) compared to cells cultured at 33.5° C. (FIG. 5, panels A and B), this difference may be at the limit of sensitivity for this assay. In order to quantitate changes in AP activity resulting from modification of the incubation temperature or by the addition of 1,25-$(OH)_2D_3$ to the media, standard enzyme assays with hFOB 1.19 cell extracts were performed. These data (FIG. 5, panel E) showed that AP activity was 2–3 fold higher in hFOB 1.19 cells cultured at 39.5° C. compared to cells cultured at 33.5° C. In addition, treatment of hFOB 1.19 cells with 1,25-$(OH)_2D_3$ resulted in a dose-dependant increase in AP activity in cells cultured at either temperature (33.5° C. or 39.5° C.). This effect of 1,25-$(OH)_2D_3$, was relatively modest as the highest dose (100 nM) produced less than a 2 fold increase in AP activity.

8. Regulation of Osteocalcin Expression

Figure 6:
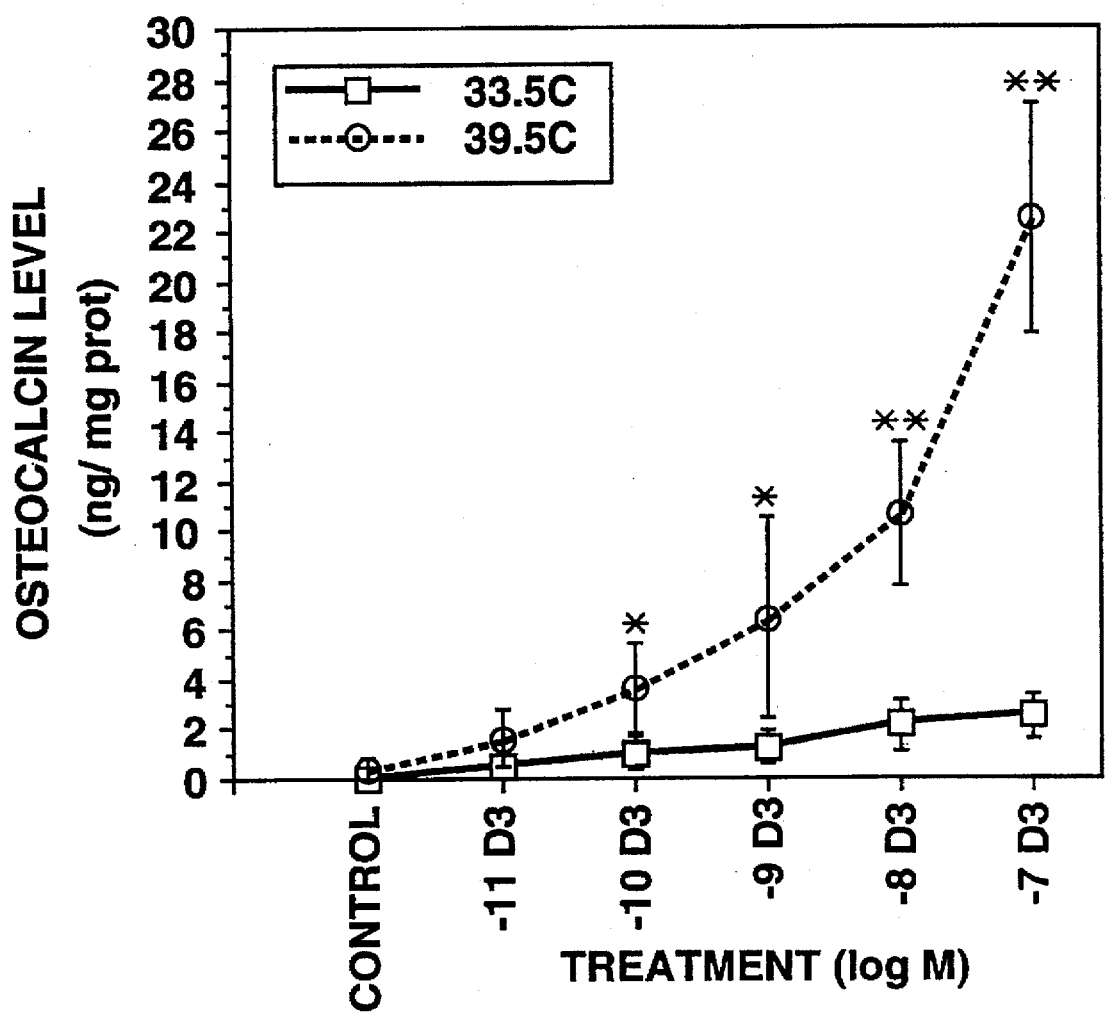
FIG. 6. Regulation of osteocalcin (OC) expression in hFOB 1.19 cells. Confluent hFOB 1.19 cells were incubated at the indicated temperatures in differentiation media (DMEM/F12 with 0.2% (v/v) charcoal-stripped FBS, 100 µg/ml ascorbic acid, and $10^{-8}$ menadione) for 24 hours, then treated for 48 hours with the indicated doses of 1,25-dihydroxy vitamin $D_3$ (1,25-$(OH)_2D_3$), or ethanol vehicle (control) at the indicated temperatures. OC levels in hFOB-conditioned media were measured by RIA using a $^{125}$I-labelled antibody to human OC and normalized to total protein in cell extracts. Error bars=1 standard deviation, n=6 experiments. *=P<0.05 39.5° C. vs 33.5° C., **=P<0.01 39.5° C. vs 33.5° C., two-tailed student's paired T test.

To determine whether hFOB 1.19 cells secrete the osteoblast specific protein osteocalcin (OC) and to determine whether OC production is regulated by 1,25-$(OH)_2D_3$ or by incubation temperature, radioimmunoassays with hFOB 1.19-conditioned media were performed. These data (FIG. 6) indicated that OC levels in hFOB 1.19-conditioned media was near or below the levels of detection without 1,25-(OH) $_2D_3$ treatment when the cells are cultured at either temperature (33.5° C. or 39.5° C.). However, treatment of hFOB 1.19 cells with 1,25-$(OH)_2D_3$ resulted in a dramatic increase in OC levels in a dose-dependant manner. Treatment with doses of 1,25-$(OH)_2D_3$ as low as 0.1 nM resulted in a notable increase in OC levels, particularly when the cells were cultured at 39.5° C. Similarly, treatment with higher doses of 1,25-$(OH)_2D_3$ resulted in correspondingly higher levels of OC. Interestingly, the effect of 1,25-$(OH)_2D_3$ on OC levels was more pronounced when the hFOB 1.19 cells were cultured at 39.5° C. In fact, when the cells were treated with 100 nM 1,25-$(OH)_2D_3$, the level of OC secreted by cells cultured at 39.5° C. was 10 fold higher than cells cultured at 33.5° C.

D. Deposit of Cells

The immortalized human fetal cells hFOB 1.19 were deposited with the American Type Culture Collection (ATCC), 12301 Parklawn Drive, Rockville, Md. 20852 USA on Jun. 4, 1993, and assigned accession number ATCC CRL 11372.

EXAMPLE II

Construction and Characterization of Estrogen-Responsive Immortalized Human Osteoblastic Cells A. Materials Used The phenol-guanidine isothiocyanate (TRI reagent) solution for RNA isolation was purchased from Molecular Research Center (Cincinnati, Ohio), radiolabeled nucleotides and steroids such as [α-$^{32}$P]-dCTP (deoxycytidine triphosphate), [$^3$H]-17β-estradiol; and [$^3$H]-R5020 (progesterone receptor agonist) were purchased from Dupont-NEN (Boston, Mass.). The cloning vector pBluescript SK and Quickhyb buffer were purchased from Stratagene (La Jolla, Calif.), and Geneticin from Gibco-BRL (Gaithersburg, Md.). Tissue culture media, 10× trypsin-EDTA reagent, and unlabeled 17β-estradiol were purchased from Sigma Chemical (St. Louis, Mo.). Hygromycin B and fetal bovine serum was purchased from Flow-ICN (Costa Mesa, Calif.). Restriction enzymes were purchased from Boehringer Mannheim Biochemicals (Indianapolis, Ind.).

B. Methods Used

1. Vector Construction

Figure 7:
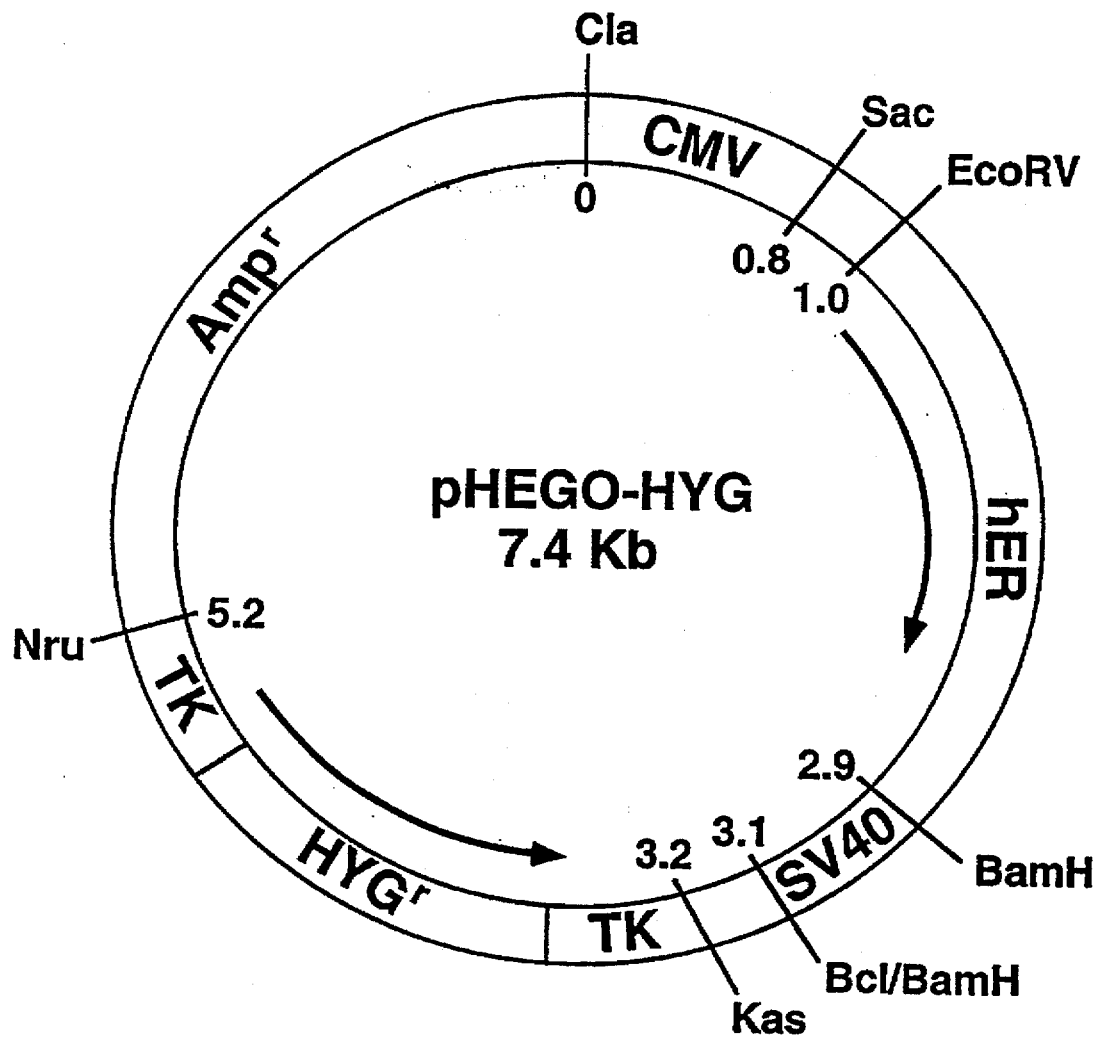
FIG. 7. Construction of the pHEGO-HYG vector. The human estrogen receptor (hER) cDNA was inserted upstream of the CMV promoter and downstream of the SV40 polyadenylation signal. The direction of transcription for the ER and hygromycin resistance (HYG$^r$) genes are indicated with arrows. Selected restriction enzyme sites are denoted (Cla=ClaI, Sac=SacI, BamH=BamHI, Bcl=BclI, Kas=KasI, Nru=NruI), as well as the map location (in Kilobase pairs from the ClaI site).

Vector construction was accomplished utilizing standard molecular biology procedures known to one skilled in the art. See, e.g., Current Protocols in Molecular Biology; F. M. Ausubel et al., Eds.; John Wiley & Sons: New York, N.Y.; 1989. Briefly, the cDNA sequence coding for the wild type human estrogen receptor (ER) was excised using EcoRI from the HEGO vector (L. Tora et al., EMBO J., 8, 1981–1986 (1989)). This 1.9 Kb fragment was ligated into the EcoRI site of the pBluescript SK vector and excised once again using EcoRV and BamHI. This fragment was ligated into the EcoRV and BamHI sites of the expression vector p636, a derivative of pHYG (B. Sudgen et al., Mol. Cell. Biol., 5, 410–413 (1985)) containing the CMV promoter (D. R. Thomsen et al., Proc. Natl. Acad. Sci. USA, 81, 659–663 (1984)) inserted into the ClaI/HindIII sites, the SV40 polyadenylation signal (BamHI/BclI fragment) inserted into the BamHI site, and the hygromycin B resistance gene driven by the thymidine kinase promoter. The ER expression vector resulting from the insertion of the ER cDNA into the p636 vector was designated pHEGO-HYG (see FIG. 7 for plasmid map).

2. Stable Transfection

Clonal hFOB 1.19 (Example I) cells were transfected with the ER expression vector pHEGO-HYG (ATCC deposit #79994) by electroporation as described in Example I. Briefly, 10 μg of pHEGO-HYG vector (linearized with NruI) was added to the transfection mixture prior to electroporation. Transfected cells were plated in growth media (Delbecco's modified Eagles medium (DMEM)/Ham F12 medium (F12) 1:1 v/v supplemented with 10% v/v charcoal stripped fetal bovine serum (csFBS)) and incubated at 33.5° C. for 48 hours, then incubated in selective media containing 150 μg/ml hygromycin B for 7–10 days until resistant colonies were clearly visible. Resistant colonies (~200–400 cells) were trypsinized in glass cloning cylinders as described in Example I. They were passaged and maintained in selective media containing 100 μg/ml hygromycin B until sufficient numbers of cells (~2×10$^7$) were obtained for cryopreservation. Routine growth conditions included media changes every 2 days and changes to selective media containing 300 μg/ml Geneticin (G418 neomycin) instead of hygromycin B were performed every alternate media change to maintain neomycin resistance.

3. Steroid Binding Assays

Specific 17β-estradiol ($E_2$) and progesterone (Pg) binding in hFOB/ER cells (i.e., cells that have been transfected with pHEGO-HYG) was measured using the micro nuclear binding (NB) assay (D. S. Colvard et al., *Clin. Chem.*, 34, 363–369 (1988)) and the dextran-coated charcoal (DCC) assay (S. N. Thibobodeau, et al., *Clin. Chem.*, 27 687–691 (1981)). Briefly, hFOB/ER cells were grown to confluence in DMEM/F12+10% (v/v) csFBS. The cells were then rinsed three times with serum free media (DMEM/F12+0.25% (w/v) BSA), treated with 10$^{-9}$M 17β-estradiol or ethanol vehicle in serum free media for 48 hours, and treated again in fresh serum free media for another 48 hours. Following the 96 hour treatment period, the cells were rinsed three times with phosphate buffered saline (PBS), removed from the tissue culture flasks by trypsin/EDTA treatment, rinsed with 10 volumes of DMEM/F12+10% (v/v) csFBS medium at 4° C., and centrifuged at 900×g for 10 minutes at 4° C. The cell pellet was rinsed with 10 ml of PBS and centrifuged at 900×g for 10 minutes at 4° C. again. The resultant cell pellets containing 4–8×10$^6$ cells for the nuclear binding assay or 40–60×10$^6$ cells for the DCC assay were incubated with radiolabeled steroids as described previously (D. S. Colvard et al., *Clin. Chem.*, 34 363–369 (1988); S. N. Thibobodeau et al., *Clin. Chem.*, 27 687–691 (1981)).

4. Northern Analyses

Total RNA was isolated from hFOB/ER cells by phenol/guanidine isothiocyanate method of P. A. Chomczynski (*Biotechniques*, 15, 532–536 (1993)), except that an additional extraction with one volume of chloroform was added after the phenol extraction. Purified RNA samples were denatured in glyoxal/dimethyl sulfoxide buffer and separated by glyoxal-agarose gel electrophoresis (G. K. McMaster et al., *Proc. Natl. Acad. Sci. USA*, 74, 4835–4838 (1977)). The RNA was then blotter to nylon filters by capillary diffusion in 20× SSC (3M NaCL, 0.3M sodium citrate ph 7.0), and bound to nylon by vacuum baking at 80° C. for two hours. Hybridization was performed in a hybridization incubator at 65° C. for two hours in 10 ml Quickhyb buffer containing 100 μg/ml denatured calf thymus DNA. Each hybridization contained approximately 10$^7$ cpm (5–10 ng) of $^{32}$P-labeled cDNA. Labeling of cDNAs was performed with a random primer labeling kit (Dupont-NEN, Boston, Mass.) in accordance with the manufacturer's instructions using [$^{32}$P]-dCTP (3000 Ci/mmol), and the labeled cDNAs were then purified by gel filtration chromatography. The northern blots were exposed to Kodak X-OMAT AR5 film with intensifying screens at −70° C. then developed in a Kodak X-OMAT M20 film processor. Quantitation of band intensities were performed with a Shimadzu (Kyoto, Japan) CS 9000 flying spot scanning laser densitometer.

C. Results

Figure 8:
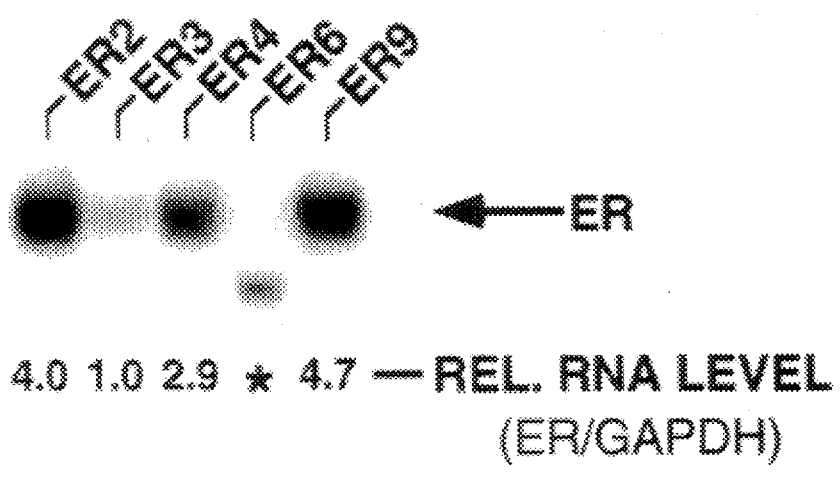
FIG. 8. Northern analysis of the hFOB/ER subclones. Total RNA (10 µg) isolated from the indicated hFOB/ER subclones was fractionated by glyoxal-agarose electrophoresis, blotted to a nylon filter, and hybridized with the ER and glyceraldehyde 3-dehydrogenase (GAPDH) cDNA probes. The ER mRNA steady state levels were determined by densitometry of the autoradiogram, normalized to GAPDH levels, and expressed as a ratio (ER/GAPDH) of relative mRNA levels (REL. RNA LEVEL). *—Indicates a truncated size ER mRNA.
Figure 8:
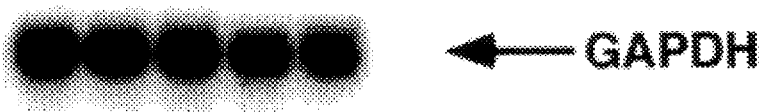

1. Expression of Estrogen Receptor (ER) and $E_2$ Binding Activity in hFOB/ER Subclones Following stable transfection of the ER expression vector pHEGO-HYG (FIG. 7) into hFOB 1.19 cells, the hFOB/ER subclones were screened for expression of ER mRNA by northern analysis. Five subclones of hFOB/ER cells were found to express significant amounts of the expected 1.9 Kb ER mRNA (FIG. 8). A broad range of ER steady state mRNA levels were expressed in the hFOB/ER subclones. The highest level of ER mRNA expression was in hFOB/ER9, which was ~5 fold more than the level of ER mRNA expression in hFOB/ER3, which had the lowest level. The hFOB/ER6 subclone expressed an aberrant size mRNA, so this subclone was not examined further.

To determine if the hFOB/ER cells exhibited functional estrogen binding, nuclear binding assays were performed with each subclone. These data (Table 2) showed that the number of estrogen binding sites in each subclone was proportional to the amount of ER mRNA expressed in each subclone, with the highest number of $E_2$ binding sites (9,799) in hFOB/ER9, and the lowest number (825) in hFOB/ER3. Untransfected cells exhibited receptor binding of less than 200 activated receptors per nucleus. Since the hFOB/ER9 cells contained the highest number of $E_2$ binding sites, this subclone was examined further for estrogen responsiveness. DCC assays performed using hFOB/ER9 cells measured ER at a level of 312 (±29 SEM from three separate assays) fmol/mg cystolic protein in this subclone. Base level ER expression in untransfected cells is not determinable using the DCC assay because it is below the sensitivity limit. DCC assays were not performed on subclones ER2, ER3, and ER4.

TABLE 2

| Subclone | Untransfected Cells | ER2 | ER3 | ER4 | ER9 |
|---|---|---|---|---|---|
| Relative RNA level[a] | N.A. | 4.0 | 1.0 | 2.9 | 4.7 |
| Relative estrogen binding[b] | N.A. | 3.7 | 1.0 | 3.7 | 11.9 |
| Activated ERs per nucleus[c] | <200 | 3,076 ± 280 | 825 ± 18 | 3,082 ± 967 | 9,799 ± 860 |

[a]Arbitrary densitometry units from northern blots using ER/GAPDH ratio.
[b]Arbitrary units corresponding to relative amount of [$^3$H]-17β-estradiol molecules/nucleus.
[c]Number of bound 17β-estradiol molecules in nucleus; 1:1 stoichiometry for $E_2$:ER. Values are ± standard deviation (n = 4 determinations).

2. Effect of $E_2$ on Progesterone Receptor (PR) Levels in Subclone hFOB/ER9

Figure 9B:
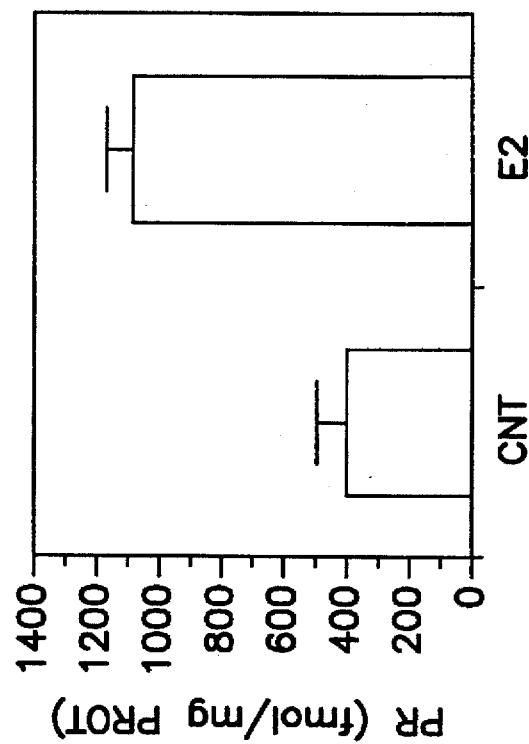
FIG. 9. Analysis of 17β-estradiol ($E_2$) effects on progesterone receptor levels in hFOB/ER9 cells. The amount of specific progesterone binding was measured in control (CNT) or $E_2$-treated hFOB/ER9 cells by the micro nuclear binding assay (panel A) or the dextran coated charcoal assay (panel B) as described in the examples section. Control and $E_2$ treatments were ethanol vehicle and $10^{-9}$M $E_2$, respectively, for 96 hours. Each bar denotes the mean value from three separate assays +/− SEM.
Figure 9A:
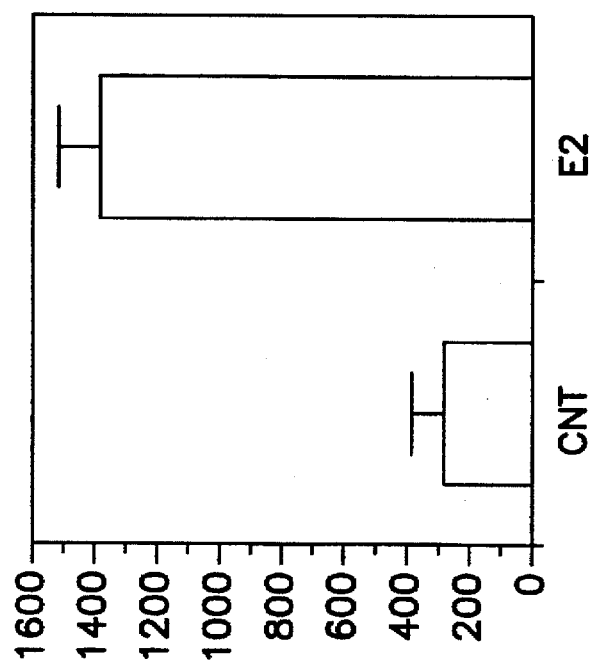

$E_2$ treatment of normal human osteoblast-like (hOB) cells is known to result in increased levels of endogenous PR expression (E. F. Erickson et al., *Science*, 241, 84–86 (1988)). To determine if endogenous PR expression is upregulated in $E_2$-treated hFOB/ER cells, nuclear binding and DCC assays were performed using the hFOB/ER9 subclone. These data (FIG. 9) indicated that the number of progesterone binding sites localized to the nucleus increased ~4 fold following treatment with 10$^{-9}$M $E_2$ as measured by the nuclear binding assay (FIG. 9, panel A). Similarly, the number of total cellular progesterone receptors increased ~2.5 fold, as measured by the DCC assay (FIG. 9, panel B).

3. Effect of $E_2$ on c-fos mRNA Levels in Subclone hFOB/ER9

Figure 10:
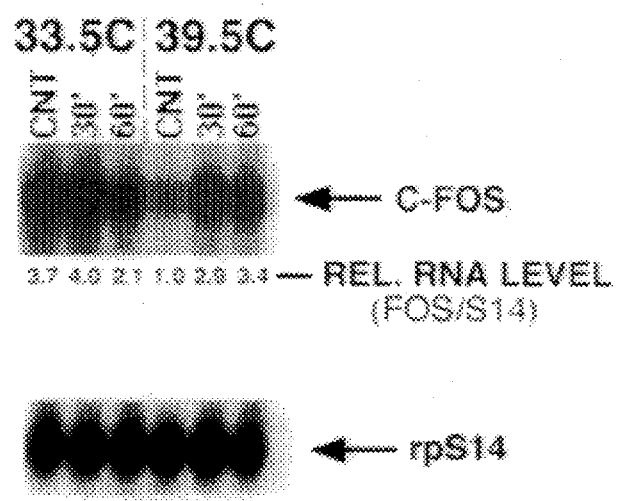
FIG. 10. Northern analysis of $E_2$ effects on c-fos mRNA levels. Total RNA (10 µg) was isolated from control (CNT) and $E_2$-treated hFOB/ER cells cultured at the indicated temperatures (33.5° C. and 39.5° C.). Control cells were treated with ethanol vehicle for 30 minutes, whereas $E_2$ treatments were for 30 or 60 minutes as denoted. Following gel electrophoresis and northern blotting, the RNA was hybridized to c-fos and ribosomal protein S14 (rpS14) cDNA probes. The relative mRNA level (REL. RNA LEVEL) as measured by densitometry was expressed as a ratio (FOS/S14).

$E_2$ treatment of hOB cells is known to result in a rapid increase in endogenous c-fos steady state mRNA level (S. A. Harris et al., *J. Bone and Mineral Res.*, 7, 57 (1992)). To examine whether $E_2$ treatment of hFOB/ER cells has a similar effect on c-fos expression, northern analyses using the hFOB/ER9 subclone were performed. These data (FIG. 10) showed that the steady state level of endogenous c-fos mRNA increased ~3 fold within 30–60 minutes of $E_2$ ($10^{-8}$M) treatment of quiescent hFOB/ER9 cells cultured at 39.5° C. Interestingly, the basal (control) level of c-fos mRNA was ~4 fold higher in hFOB/ER cells maintained at 33.5° C. than cells at 39.5° C. In addition no significant increase in the level of c-fos mRNA occurred in cells cultured at 33.5° C.

D. Deposit of Vector

The ER plasmid pHEGO-HYG was deposited with the American Type Culture Collection (ATCC), 12301 Parklawn Drive, Rockville, Md. 20852 USA on Apr. 20, 1994, and assigned accession number 79994 for the plasmid in *E. coli* HB 101 and 79995 for purified plasmid DNA.

The complete disclosure of all patents, patent documents, and publications cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. An immortalized normal human fetal osteoblastic cell which expresses a temperature sensitive mutant of simian virus 40 large T protein antigen and human estrogen receptor.

2. A homogeneous population of cells comprising the immortalized normal human fetal osteoblastic cell of claim 1.

3. The population of claim 2 which is a clonal population.

4. The population of claim 2 which is nontumorigenic.

5. The immortalized normal human fetal osteoblastic cell of claim 1 wherein the T antigen is inactivated at a restrictive temperature.

6. The immortalized normal human fetal osteoblastic cell of claim 5 wherein the T antigen is either cycled between an inactive and an active state or not cycled between an inactive and an active state.

7. The immortalized normal human fetal osteoblastic cell of claim 1 which undergoes osteoblastic differentiation.

8. The immortalized normal human fetal osteoblastic cell of claim 1 which expresses human estrogen receptor at a level greater than about 400 activated receptors per nucleus.

9. An immortalized normal human fetal osteoblastic cell which expresses human estrogen receptor, prepared by a process comprising (a) transfecting a human fetal bone cell with a gene coding for a temperature sensitive mutant of simian virus 40 large T antigen, and (b) transfecting the human fetal bone cell with a gene coding for human estrogen receptor; wherein step (b) is performed before, after, or concurrent with step (a).

10. The immortalized normal human fetal osteoblastic cell of claim 9 which expresses human estrogen receptor at a level greater than about 400 activated receptors per nucleus.

11. The immortalized normal human fetal osteoblastic cell of claim 9 wherein the gene coding for human estrogen receptor is located on a replicable expression vector.

12. The immortalized normal human fetal osteoblastic cell of claim 11 wherein the replicable expression vector is a plasmid.

13. The immortalized normal fetal osteoblastic cell of claim 12 wherein the plasmid has the identifying characteristics of pHEGO-HYG (ATCC No. 79995).

14. The immortalized normal fetal osteoblastic cell of claim 13 wherein the plasmid is pHEGO-HYG (ATCC No. 79995).

15. The immortalized normal human fetal osteoblastic cell of claim 9 wherein the gene coding for a temperature sensitive mutant of simian virus 40 large T antigen is located on expression vector pUCSVtsA58.

16. The immortalized normal human fetal osteoblastic cell of claim 9 wherein the process further comprises (c) transfecting the human fetal bone cell with a gene coding for a selectable marker; wherein step (c) is performed before, after, or concurrent with steps (b) and (c).

17. The immortalized normal human fetal osteoblastic cell of claim 16 wherein the gene for the selectable marker is located on expression vector pSV2neo.

18. An immortalized normal human fetal osteoblastic cell that expresses human estrogen receptor at a level greater than about 400 activated receptors per nucleus.

19. A method of preparing an immortalized normal human fetal osteoblastic cell which expresses human estrogen receptor comprising:

(a) isolating a bone cell from human fetal tissue;

(b) transfecting the isolated human fetal bone cell with an expression vector comprising a gene coding for a temperature sensitive mutant of simian virus 40 large T antigen; and (c) transfecting the isolated human fetal bone cell with an expression vector comprising a gene coding for human estrogen receptor;

wherein step (c) is performed before, after, or concurrent with step (b).

20. The method of claim 19 further comprising (d) transfecting the isolated human fetal bone cell with a gene encoding a selectable marker, wherein step (d) is performed before, after, or concurrent with steps (b) and (c).

21. The method of claim 19 wherein the immortalized normal human fetal osteoblastic cell expresses human estrogen receptor at a level greater than about 400 activated receptors per nucleus.

22. The method of claim 19 wherein the expression vector comprising a gene coding for a human estrogen receptor is a plasmid having the identifying characteristics of pHEGO-HYG (ATCC No. 79995).

23. The method of claim 22 wherein the plasmid is pHEGO-HYG (ATCC No. 79995).

24. A replicable expression vector which has the identifying characteristics of pHEGO-HYG (ATCC No. 79995).

25. The vector of claim 24 which is pHEGO-HYG (ATCC No. 79995).

* * * * *